(12) United States Patent
Dohil et al.

(10) Patent No.: US 8,497,258 B2
(45) Date of Patent: *Jul. 30, 2013

(54) VISCOUS BUDESONIDE FOR THE TREATMENT OF INFLAMMATORY DISEASES OF THE GASTROINTESTINAL TRACT

(75) Inventors: Ranjan Dohil, San Diego, CA (US); John Bastian, San Diego, CA (US); Seema Aceves, Solana Beach, CA (US); Elaine Phillips, San Diego, CA (US); Malcolm Hill, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 788 days.

This patent is subject to a terminal disclaimer.

(21) Appl. No.: 12/269,693

(22) Filed: Nov. 12, 2008

(65) Prior Publication Data

US 2009/0191275 A1 Jul. 30, 2009

Related U.S. Application Data

(63) Continuation-in-part of application No. 11/595,513, filed on Nov. 9, 2006.

(60) Provisional application No. 60/735,340, filed on Nov. 12, 2005, provisional application No. 61/090,575, filed on Aug. 20, 2008.

(51) Int. Cl.
*A61K 31/56* (2006.01)

(52) U.S. Cl.
USPC ............................................ 514/171; 514/182

(58) Field of Classification Search
USPC .................................................. 514/182, 171
See application file for complete search history.

(56) References Cited

U.S. PATENT DOCUMENTS

| 2,861,920 | A | * | 11/1958 | Dale et al. ....................... 514/39 |
|---|---|---|---|---|
| 4,684,534 | A | | 8/1987 | Valentine |
| 4,900,552 | A | | 2/1990 | Sanvordeker et al. |
| 4,985,418 | A | | 1/1991 | Richards |
| 5,288,497 | A | | 2/1994 | Stanley et al. |
| 5,446,070 | A | | 8/1995 | Mantelle |
| 5,585,108 | A | | 12/1996 | Ruddy |
| 5,607,662 | A | | 3/1997 | Baskeyfield et al. |
| 5,643,602 | A | | 7/1997 | Ulmius |

(Continued)

FOREIGN PATENT DOCUMENTS

| EP | 1201242 A2 | 5/2002 |
|---|---|---|
| EP | 1428526 A1 | 12/2002 |

(Continued)

OTHER PUBLICATIONS

Martin, Physical Pharmacy, 4th edition, p. 423, 1993, published by Lea & Febiger.*

(Continued)

*Primary Examiner* — San-Ming Hui
(74) *Attorney, Agent, or Firm* — Kilpatrick Townsend & Stockton LLP

(57) ABSTRACT

Provided herein are methods for preventing or alleviating the symptoms of and inflammation associated with inflammatory diseases and conditions of the gastrointestinal tract, for example, those involving the esophagus. Also provided herein are pharmaceutical compositions useful for the methods of the present invention.

13 Claims, 5 Drawing Sheets

U.S. PATENT DOCUMENTS

| | | | |
|---|---|---|---|
| 5,711,936 A | 1/1998 | Hill et al. | |
| 5,763,910 A * | 6/1998 | Ema | 257/296 |
| 5,814,330 A | 9/1998 | Putteman et al. | |
| 5,837,713 A | 11/1998 | Gleich | |
| 5,863,910 A | 1/1999 | Bolonick et al. | |
| 5,889,028 A | 3/1999 | Sandborn et al. | |
| 6,028,095 A | 2/2000 | Guglietta | |
| 6,291,445 B1 | 9/2001 | Nilsson et al. | |
| 6,306,789 B1 | 10/2001 | Dettmar et al. | |
| 6,348,502 B1 | 2/2002 | Gardiner et al. | |
| 6,387,383 B1 | 5/2002 | Dow et al. | |
| 6,509,028 B2 | 1/2003 | Williams et al. | |
| 6,562,363 B1 | 5/2003 | Mantelle et al. | |
| 6,589,551 B1 | 7/2003 | Jolliffe | |
| 6,589,556 B2 | 7/2003 | Cherukuri | |
| 6,596,261 B1 | 7/2003 | Adjei et al. | |
| 6,638,521 B2 | 10/2003 | Dobrozsi | |
| 6,787,529 B2 | 9/2004 | Hoy et al. | |
| 6,899,099 B2 | 5/2005 | Andersson et al. | |
| 6,916,485 B2 | 7/2005 | Aiache et al. | |
| 6,923,988 B2 | 8/2005 | Patel et al. | |
| 6,986,904 B2 | 1/2006 | Nilsson et al. | |
| 7,063,862 B2 | 6/2006 | Lin et al. | |
| 7,229,641 B2 | 6/2007 | Cherukuri | |
| 7,288,267 B2 | 10/2007 | Bosch et al. | |
| 7,361,646 B2 | 4/2008 | Belanoff | |
| 7,544,348 B2 | 6/2009 | Jacob et al. | |
| 7,547,433 B2 | 6/2009 | Jacob et al. | |
| 2001/0016577 A1 | 8/2001 | Dobrozsi et al. | |
| 2001/0029255 A1 | 10/2001 | Lindberg et al. | |
| 2001/0049366 A1 | 12/2001 | Singh | |
| 2002/0132803 A1 | 9/2002 | Dedhya et al. | |
| 2002/0168334 A1 | 11/2002 | Jacob et al. | |
| 2003/0013693 A1 | 1/2003 | Guiverc'h et al. | |
| 2003/0017189 A1 | 1/2003 | Wong et al. | |
| 2003/0055028 A1 | 3/2003 | Stergioupoulos et al. | |
| 2003/0073676 A1 | 4/2003 | Biggadike et al. | |
| 2003/0192533 A1 | 10/2003 | Andersson et al. | |
| 2003/0215496 A1 | 11/2003 | Patel et al. | |
| 2004/0023935 A1 | 2/2004 | Banerjee et al. | |
| 2004/0028919 A1 | 2/2004 | Yamamoto et al. | |
| 2004/0053894 A1 | 3/2004 | Mazess et al. | |
| 2004/0141949 A1 | 7/2004 | Rosenthal et al. | |
| 2005/0042282 A1 | 2/2005 | Leni | |
| 2005/0049459 A1 | 3/2005 | Hern | |
| 2005/0079138 A1 * | 4/2005 | Chickering et al. | 424/46 |
| 2005/0152847 A1 | 7/2005 | Trofast et al. | |
| 2005/0153946 A1 | 7/2005 | Hirsh et al. | |
| 2005/0208110 A1 | 9/2005 | Singh et al. | |
| 2005/0239845 A1 | 10/2005 | Proehl et al. | |
| 2005/0281772 A1 | 12/2005 | Bromley et al. | |
| 2005/0287181 A1 | 12/2005 | Murthy | |
| 2006/0013873 A1 | 1/2006 | Yang et al. | |
| 2006/0024238 A1 | 2/2006 | Barth | |
| 2006/0128655 A1 | 6/2006 | Falk et al. | |
| 2006/0193783 A1 | 8/2006 | Bhowmick et al. | |
| 2006/0216353 A1 | 9/2006 | Liversidge et al. | |
| 2006/0235053 A1 | 10/2006 | Gebauer | |
| 2007/0031459 A1 | 2/2007 | Asotra | |
| 2007/0111978 A1 | 5/2007 | Dohil et al. | |
| 2007/0134280 A1 | 6/2007 | Roman et al. | |
| 2007/0248548 A1 | 10/2007 | Blondino et al. | |
| 2007/0259037 A1 | 11/2007 | Guiverc'h et al. | |
| 2008/0008762 A1 | 1/2008 | Robinson et al. | |
| 2008/0132580 A1 | 6/2008 | Mandavilli et al. | |
| 2008/0207771 A1 | 8/2008 | Dikstein | |
| 2009/0123390 A1 | 5/2009 | Hill et al. | |
| 2009/0123550 A1 | 5/2009 | Phillips et al. | |
| 2009/0123551 A1 | 5/2009 | Phillips et al. | |
| 2009/0131386 A1 | 5/2009 | Phillips et al. | |
| 2009/0137540 A1 | 5/2009 | Phillips et al. | |
| 2009/0143343 A1 | 6/2009 | Hill et al. | |
| 2009/0149433 A1 | 6/2009 | Phillips et al. | |
| 2009/0181099 A1 | 7/2009 | Dohil et al. | |
| 2009/0264392 A1 | 10/2009 | Warndahl | |

FOREIGN PATENT DOCUMENTS

| | | |
|---|---|---|
| EP | 1795183 A1 | 8/2006 |
| WO | WO99/18938 A1 | 4/1999 |
| WO | WO99/32156 A2 | 7/1999 |
| WO | WO99/39699 | 8/1999 |
| WO | WO99/40906 | 8/1999 |
| WO | WO00/10528 | 3/2000 |
| WO | WO01/37808 | 5/2001 |
| WO | WO01/41748 | 6/2001 |
| WO | WO02/24205 | 3/2002 |
| WO | WO02/34235 | 5/2002 |
| WO | WO02/064113 | 8/2002 |
| WO | WO02/074316 | 9/2002 |
| WO | WO03/057194 | 7/2003 |
| WO | WO2004/030652 | 4/2004 |
| WO | WO2004/045612 A1 | 6/2004 |
| WO | WO2004/069225 | 8/2004 |
| WO | WO2004/082590 | 9/2004 |
| WO | WO2005/056066 | 6/2005 |
| WO | WO2005/065185 | 7/2005 |
| WO | WO2005/074930 | 8/2005 |
| WO | WO2005/120517 | 12/2005 |
| WO | WO2006/009825 | 1/2006 |
| WO | WO2006/035418 A2 | 4/2006 |
| WO | WO2006/048736 A1 | 5/2006 |
| WO | WO2006/085101 A2 | 8/2006 |
| WO | WO2006/099591 A1 | 9/2006 |
| WO | WO2007/061803 | 5/2007 |
| WO | WO2007/075475 | 7/2007 |
| WO | WO2007/096906 | 8/2007 |
| WO | WO2008/070129 A2 | 6/2008 |
| WO | WO2008/091855 | 7/2008 |

OTHER PUBLICATIONS

Batchelor et al., "An in vitro mucosal model for prediction of the bioadhesion of alginate solutions to the oesophagus", International Journal of Pharmaceutics, vol. 238 (2002) pp. 123-132.

Batchelor et al., "Feasiblity of a bioadhesive drug delivery system targeted to oesophageal tissue", European Journal of Pharmaceutics and Biopharmaceutics, vol. 57 (2004) pp. 295-298.

Batchelor, "Bioadhesive dosage forms for esophageal drug delivery", Pharmaceutical Research, vol. 22, No. 2, Feb. 2005 (2004) pp. 175-181.

Christrup et al., "Deposition of a model substance, 99mTc E-HIDA, in the oral cavity after administration of lozenges, chewing gum and sublingual tablets", International Journal of Pharmaceutics, vol. 66, (1990) pp. 169-174.

Dobrozsi et al., "Comparative mucoretention of sucralfate suspensions in an everted rat esophagus model", Internation Journal of Pharmaceutics, vol. 189 (1999) pp. 81-89.

Hardy et al., "A comparison of the gastric retention of a sucralfate gel and a sucralfate suspension", Eur. J. Biopharm., vol. 39(2) (1991) pp. 70-74.

Laine et al., "Prospective study of fluconazole suspension for the treatment of oesophageal candidiasis in patients with AIDS", Aliment Pharmacol Ther. 1995:9, pp. 553-556.

Martins et al., "Fluconazole suspension for oropharyngeal candidiasis unresponsive to tablets", Annals of Internal Medicine, vol. 126, No. 4 (Feb. 15, 1997) pp. 332-333.

Potts et al., "In vivo determination of the oesophageal retention of smart hydrogel™", Proceedings International Symp. Control. Rel. Bioact. Mater., 24 (1997), Controlled Release Society, Inc., pp. 335-336, 3 pages total.

Richardson et al., "Oesophageal bioadhesion of sodium alginate suspensions: particle swelling and mucosal retention", European Journal of Pharmaceutical Sciences, vol. 23 (2004) pp. 49-56, available online Jul. 10, 2004.

Smart et al., "The retention of 14C-labelled poly (acrylic acids) on gastric and oesophageal mucosa: an in vitro study", European Journal of Pharmaceutica Sciences, vol. 20 (2003) pp. 83-90.

Tang et al., "Bioadhesive oesophageal bandages: protection against acid and pepsin injury", International Journal of Pharmaceutics, vol. 292 (2005) pp. 169-177.

Wise et al., "Regional differences in oesophageal motor function", Neurogastroenterol Motil Blackwell Publishing Ltd. (2004) 16, pp. 31-37.

Young et al., "A novel in-vitro apparatus for evaluating the mucoadhesion of liquid and semi-solid formulations", J. Pharm. Pharmacol. (1998), 50 (Supplement), p. 167, 1 page total.

Zhang et al., "A bioadhesive formulation for the delivery of antifungal agents to the oesophagus", JJP (2004), 56 (Supplement), S-16, 1 page total.

Aceves et al., "Prospective Analysis of an Abdominal Symptom Scoring Tool's Efficacy in the Clinical Distinction of Pediatric Eosinophilic Esophagitis from Gastroesophageal Reflux Disease," J. Allergy Clin. Immunol. Feb. 2008, S70 Abstracts No. 270.

Aceves, S et al., "Distinguishing Eosinophilic Esophagitis in pediatric patients: clinical, endoscopic, and histologic features of an emerging disorder," Journal of Clinical Gastroenterology 2006; 41(3):252-6.

Aceves, SS et al. "Topical viscous budesonide suspension for treatment of eosinophilic esophagitis," J. Allergy Clin. Immunol. 2005; 116(3):705-6.

Aceves, SS et al., "Oral viscous budesonide: a potential new therapy for eosinophilic esophagitis in children," Amer. Journal of Gastroenterology 2007; 102:1-9.

Ashorn et al., "The Natural Course of Gastroesophageal Reflux Disease in Children," Scand. J. Gastroenterol. 37(6):638-641 (2002).

Blanchard et al., "Eotaxin-3 and a uniquely conserved gene-expression profile in eosinophilic esophagitis," J. Clin Invest. 116(2):536-547 (2006).

Bogaart, H.C.A. et al., "Viscosity Is Not a Parameter of Postdeglutitve Pharyngeal Residue: Quantification and Analysis with Scintigraphy," Dysphagia 22:145-149 (2007).

Bonis, P. et al., "Eosinophilic esophagitis," downloaded from the internet on Aug. 7, 2008 at http://www.uptodate.com/online/content/topic.do?topicKey=eso_dis/11927&view=print.

Budin, C et al. "Eosinophilic esophagitis: 3 case reports," Gastroenterol. Clin. Biol. 2005; 29:73-5.

Campieri et al., "Oral budesonide is as effective as oral prednisolone in active Crohn's disease," Gut 41:209-214 (1997).

Caro, J.J. et al., "Healing and relapse rates in gastroesophageal reflux disease treated with the newer proton-pump inhibitors lansoprazole, rabeprazole, and pantoprazole compared with omeprazole, ranitidine, and placebo: evidence from randomized clinical trials," Clin. Thera. 23(7):998-1017 (2001).

Cherian S et al., "Rapidly increasing prevalence of eosinophilic oesophagitis in Western Australia," Arch. Dis. Child 2006; 91:1000-4.

Cheung, K M et al., "Esophageal eosinophilia in children with dysphagia," J. Pediatr. Gastroenterol. Nutr. 2003;37:498-503.

Collaud, S. et al., "Clinical evaluation of bioadhesive hydrogels for topical delivery of hexylaminolevulinate to Barrett's esophagus," J. Controlled Release 123:203-210 (2007).

Croese J et al., "Clinical and endoscopic features of eosinophilic esophagitis in adults," Gastrointest. Endosc. 2003; 58(4):516-22.

Desai T K et al., "Association of eosinophilic inflammation with esophageal food impaction in adults," Gastrointest. Endosc. 2005; 61(7):795-801.

Dohil R et al., "The evaluation and treatment of gastrointestinal disease in children with cystinos is receiving cysteamine," J. Pediatr. 2003; 14:224-30.

Faubion W A, Jr. et al., "Treatment of eosinophilic esophagitis with inhaled corticosteroids," J. Pediatr. Gastroenterol. Nutr. 1998; 27(1):90-3, downloaded from the internet on Jul. 30, 2007 at http://gateway.tx.ovid.com.proxy.lib.mcw.edu/gw1/ovidweb.cgi.

Fogg M I et al., "Pollen and eosinophilic esophagitis," J. Allergy Clin. Immunol. 2003; 112:796-7.

Fox V L et al., "Eosinophilic esophagitis: it's not just kid's stuff," Gastrointest. Endosc. 2002; pp. 1-15.

Furuta, GT et al., "Eosiniophilic esophagitis in children and adults: A systematic review and consensus recommendations for diagnosis and treatment," Gastroenterology 2007; 133:1342-63.

Garrett J K et al., "Anti-interleukin-5 (mepolizumab) therapy for hypereosinophilic syndromes," J. Allergy Clin. Immunol. 2004; 113:115-9.

GB0911779.7 Search Report dated Aug. 18, 2009, 4 pages.

Gilani, K. et al., "Aerosolisation properties of disodium cromoglycate microparticles spray dried from different water to ethanol ratio," JPP S6(Suppl.):Abstract 043 (2004).

Guajardo J R et al., "Eosinophil-associated gastrointestinal disorders: a world-wide-web based registry," J. Pediatr. 2002; 141:576-81.

Hanauer, S.B., "Therapy Update: New steroids for IBD: progress report," Gut 51:182-183 (2002).

Hellers, et al., "Oral Budesonide for Prevention of Postsurgical Recurrence in Crohn's Disease," Gastroenterol. 116:294-300 (1999).

Honkanen, O. et al., "Bioavailability and in vitro oesophageal sticking tendency of hydroxypropyl methylcellulose capsul formulations and corresponding gelatine capsul formulations," Eur. J. Pharm. Sci. 15:479-488 (2002).

Ishibashi, H. et al., "Oral administration of itraconazole solution has superior efficacy in experimental oral and oesophageal candidiasis in mice than its intragastric administration," J. Antimicrobial Chemotherapy 59:317-320 (2007).

Kagalwalla A F et al., "Effect of six-food elimination diet on clinical and histologic outcomes in eosinophilic esophagitis," Clin. Gastroenterol. Hepatol. 2006; 4:1097-102.

Karnam U. et al., "Effectiveness of oral budesonide suspension in adult patients with eosinophilic esophagitis," 1 page, downloaded from the internet on May 13, 2008 at http://download.abstractcentral.com/ddw2008/myddw2008/S1974.html.

Kelly K J et al., "Eosinophilic esophagitis attributed to gastroesophageal reflux: improvement with an amino acid-based formula," Gastroenterology 1995; 109: 1503-12.

Khan et al., "Esoinophilic Gastroenteritis. Epidemiology, Diagnosis and Management," Pediatr. Drugs 4(9):563-570 (2002).

Konikoff et al., "A Randomized, Double-Blind, Placebo-Controlled Trial of Fluticasone Propionate for Pediatric Eosinophilic Esophagitis," Gastroenterol. 131:1381-1391 (2006).

Li, W. et al., "Clinical and endoscopic features of Chinese reflux esophagitis patients," World J. Gastroenterol, Mar. 28, 2008, 14(12):1866-71.

Liacouras C A et al., "Eosinophilic esophagitis," Curr. Opin. Pediatr. 2004; 16:560-6.

Liacouras C A et al., "Eosinophilic esophagitis: a 10-year experience in 381 children," Clin. Gastroenterol. Hepatol. 2005; 3:1198-206.

Liacouras C A et al., "Primary eosinophilic esophagitis in children: successful treatment with oral corticosteroids," J. Pediatr. Gastroenterol. Nutr. 1998; 26(4):380-5.

Liacouras C A., "Eosinophilic esophagitis: treatment in 2005," Curr. Opin. Gastroenterol. 2006; 22:147-152.

Markowitz J E et al., "Elemental diet is an effective treatment for eosinophilic esophagitis in children and adolescents," Am. J. Gastroenterol. 2003; 98(4):777-82.

Mishra A et al., "An etiological role for aeroallergens and eosinophils in experimental esophagitis," J. Clin. Invest. 2001; 107(1):83-90.

Mueller S et al., "Eosinophil infiltration and degranulation in oesophageal mucosa from adult patients with eosinophilic oesophagitis: a retrospective comparative study on pathologic biopsy," J. Clin. Pathol. 2006; 59:1175-80.

Newman, S.P. et al., "New developments in radionuclide imaging for assessing drug delivery in man," Eur. J. Pharma. Sci. 18:19-22 (2003).

Nicolazzo, JA et al., "Buccal penetration enhancers—how do they really work?" J. Controlled Release 2005; 105:1-15.

Noel R J et al., "Clinical and immunopathologic effects of swallowed fluticasone for eosinophilic esophagitis," Clin. Gastroenterol. Hepatol. 2004; 2:568-75.

Noel R J et al., "Eosinophilic esophagitis," N. Engl. J. Med. 2004; 351:940-1.

Oliviera, C. et al., "Eosinophilic esophagitis and intermediate esophagitis after tracheoesophageal fistula repair: a case series," J. Ped. Surg. 43:810-814 (2008).

Orenstein S R et al., "The spectrum of pediatric eosinophilic esophagitis beyond infancy: a clinical series of 30 children," Am. J. Gastroenterol. 2000; 95(6):1422-30.

Parfitt J R et al., "Eosinophilic esophagitis in adults: distinguishing features from gastroesophageal reflux disease: a study of 41 patients," Mod. Pathol. 2006; 19:90-6.

PCT/US2008/012712 Search Report dated Jun. 25, 2009, 4 pages.
PCT/US2008/012780 Search Report dated Jun. 25, 2009, 4 pages.
PCT/US2008/012781 Search Report dated Jun. 25, 2009, 4 pages.
PCT/US2008/012783 Search Report dated Jun. 16, 2009, 4 pages.
PCT/US2008/083288 Search Report dated May 18, 2009, 4 pages.
PCT/US2008/083290 Search Report dated Jul. 15, 2009, 6 pages.
PCT/US2009/041316 Search Report and Written Opinion dated Oct. 30, 2009, 13 pages.
Plaza-Martin, Am et al., "Polysensitization to aeroallergens and food in eosinophilic esophagitis in a pediatric population," Alergol. Immunopathol. 2007; 35(1):35-7.
Potter J W et al., "Eosinophilic esophagitis in adults: an emerging problem with unique esophageal features," Gastrointest. Endosc. 2004; 59(3):355-61.
Ravelli A M et al., "Dilated Intercellular Spaces: A Major Morphological Feature of Esophagitis," J. Pediatr. Gastroenterol. Nutr. 2006; 42:510-515.
Remedios M et al., "Eosinophilic esophagitis in adults: clinical, endoscopic, histologic findings, and response to treatment with fluticasone propionate," Gastrointest. Endosc. 2006; 63(1):3-12.
Rothenberg M E, et al., "Pathogenesis and clinical features of eosinophilic esophagitis," J. Allergy Clin. Immunol. 2001; 108:891-4.
Rothenberg M E., "Eosinophilic gastrointestinal disorders (EGID)," J. Allergy Clin. Immunol. 2004; 113:11-28.
Rowe et al., "Handbook of Pharmaceutical Excipients," Pharmaceutical Press, Jan. 1, 2006, pp. 442-445.
Ruchelli E et al., "Severity of esophageal eosinophilia predicts response to conventional gastroesophageal reflux therapy," Pediatr. Dev. Pathol. 1999; 2:15-18.
Sant'Anna A M et al., "Eosinophilic Esophagitis in Children: Symptoms, Histology and pH Probe Results," J. Pediatr. Gastroenterol. Nutr. 2004; 39:373-377.
Shah, A. and Hirano, I., "Treatment of Eosinophilic Esophagitis: Drugs, Diet, or Dilation?" Curr. Gastroent. Reports 9:181-188 (2007).
Sharpe, S.A. et al., "Comparison of the Flow Properties of Aqueous Suspension Corticosteroid Nasal Sprays Under Differing Sampling Conditions," Drug Dev. Industrial Pharmacy 29(9):1005-1012 (2003).
Sicherer, S.H., "Clinical Aspects of Gastrointestinal Food Allergy in Childhood," Pediatr. 111(6):1608-1616 (2003), downloaded from the internet on Sep. 28, 20009 at www.pediatrics.org.
Spergel J M et al., "The use of skin prick tests and patch tests to identify causative foods in eosinophilic esophagitis," J. Allergy Clin. Immunol. 2002; 109:363-8.
Spergel J M et al., "Treatment of eosinophilic esophagitis with specific food elimination diet directed by a combination of skin prick and patch tests," Ann. Allergy Asthma Immunol. 2005; 95:336-43.

Spergel JM., "Eosinophilic esophagitis in adults and children: evidence for a food allergy component in many patients," Curr. Opin. Allergy Clin. Immunol. 2007; 7:274-8.
Steiner S J et al., "Correlation between number of eosinophils and reflux index on same day esophageal biopsy and 24 hour esophageal pH monitoring," Am. J. Gastroenterol. 2004; 99:801-5.
Steiner S J et al., "Severity of Basal Cell Hyperplasia Differs in Reflux Versus Eosinophilic Esophagitis," J. Pediatr. Gastroenterol. Nutr. 2006; 42:506-509.
Straumann A and Simon H U, "Eosinophilic esophagitis: escalating epidemiology?" J. Allergy Clin. Immunol. 2005; 115:418-9.
Straumann A et al., "Natural history of primary eosinophilic esophagitis: a follow-up of 30 adult patients for up to 11.5 years," Gastroenterology 2003; 125:1660-9.
Suarez, C.L. et al., "Caustic esophagitis in children," Anales Espanoles de Pediatria, Mar. 1992, 36(3):205-207, Abstract, 1 page.
Teitelbaum J E et al., "Eosinophilic esophagitis in children: immunopathological analysis and response to fluticasone propionate," Gastroenterology 2002; 122:1216-25.
Varum, F.J.O. et al., "Mucoadhesion and the Gastrointestinal Tract," Critical Reviews Ther. Drug Carrier Systems 25(3):207-258 (2008).
Watts, et al., "TARGIT™ technology coated starch capsules for site-specific drug delivery into the lower gastrointestinal tract," Exp. Op. Drug Delivery 2(1):159-167 (2005), Abstract, 1 page.
Zhang, L. et al., "Strategies and therapeutic opportunities for the delivery of drugs to the esophagus," Critical Reviews Ther. Drug Carrier Systems 25(3):259-304 (2008).
Demuth, K.A. et al., "Treatment of allergic esophagitis with budesonide turbuhaler," J. Allergy Clin. Immunol., Feb. 2004, 113(2 Suppl);S316 Abstract, 1 page.
Pulmicort Turbuhaler Monograph, AstraZeneca, Dec. 2001, 3 pages.
Fawcett, J. Paul et al., "Stability of hydrocortisone oral suspensions prepared from tablets and powder", The Annals of Pharmacotherapy, Oct. 1995, 29(10)987-90.
Furuta, Glenn T., "Eosinophils in the esophagus: acid is not the only cause", Journal of Pediatric Gastroenterology & Nutrition 26(4):468-471, Apr. 1998.
Garcia, Jane M. et al., "Viscosity measurements of nectar- and honey-thick liquids: product, liquid, and time comparisons", Dysphagia 20:325-335, 2005.
International Preliminary Report on Patentability dated Feb. 22, 2011 for International PCT Application No. PCT/US2008/083290, 7 pages.
Noureddini, Hossein, "Viscosities of vegetable oils and fatty acids", JAOCS 69(12):1189-1191, 1992.
Lotong et al., "Texture and Flavor Characteristics of Beverages Containing Commercial Thickening Agents for Dysphagia Diets", Journal of Food and Science 68(4):1537-1541, 2003.

* cited by examiner

VISCOUS BUDESONIDE FOR THE TREATMENT OF INFLAMMATORY DISEASES OF THE GASTROINTESTINAL TRACT

CROSS-REFERENCE

This application is a continuation-in-part application of Ser. No. 11/595,513, filed Nov. 9, 2006, published as US 2007/0111978 on May 17, 2007, and entitled "Viscous Budesonide for the Treatment of Inflammatory Diseases of the Gastrointestinal Tract", which is incorporated herein by reference in its entirety and to which application we claim priority under 35 USC §120, which claims priority to U.S. Provisional Application Ser. No. 60/735,340, filed Nov. 12, 2005, and entitled "Viscous Budesonide for the Treatment of Inflammatory Diseases of the Gastrointestinal Tract" which is referred to and incorporated herein by reference in its entirety.

This application also claims the benefit of U.S. Provisional Application No. 61/090,575, filed Aug. 20, 2008, which application is incorporated herein by reference.

FIELD OF THE INVENTION

The invention is in general directed to methods and pharmaceutical compositions for preventing or alleviating the symptoms of and inflammation associated with inflammatory diseases involving the esophagus.

BACKGROUND OF THE INVENTION

Esophageal inflammation disorders are gaining increased recognition in both adults and children. One example is eosinophilic esophagitis (EE or EoE), which is an emerging, and fast-growing disorder characterized by high levels of eosinophils in the esophagus, as well as basal zone hyperplasia. EE is thought to be provoked, in at least a subset of patients, by food allergies or airborne allergen exposure (1-5, 44). EE diagnosis is often associated with other hypersensitivity disorders, including asthma, rhinitis, and other food and aeroallergen inhalant sensitivities (39-40). Diagnosis is often made, e.g., in young children and depends on the finding of 15 to 20 or more to 24 or more eosinophils per high power field (eos/hpf) within esophageal mucosal biopsies (6-12).

In parallel with other atopic disorders, the incidence of EE appears to be increasing (15, 35). The disorder may present with reflux-like symptoms, pain and dysphagia, clinical symptoms similar to the presentation of gastroesophageal reflux disease ("GERD") (42). Symptoms of EE may include, for example, one or more of the following: abdominal pain, chest pain, choking, difficulty swallowing, failure to thrive, nausea, reflux not relieved by standard anti-flux therapy, skin rash or hives, vomiting, and weight loss. In one series, 15% of EE patients had concurrent developmental delay (45).

Although EE is becoming more frequently diagnosed throughout developing countries (7, 8, 13-16) many aspects of the disease remain unclear including its etiology, natural history and optimal therapy. Symptoms of EE often mimic those of GERD and include vomiting, dysphagia, pain and food impaction (8, 14, 17-20). However, treatment of EE and GERD differ and it is important to distinguish between them, particularly as untreated EE may be associated with esophageal narrowing in 10-30% of cases (14, 18, 20, 21). The common occurrence regarding misdiagnosis of EE for GERD often results in delayed treatment for patients with EE. (42).

Long term systemic steroid therapy can result in significant secondary side effects on growth and bone development, therefore topical steroid formulations are often used to treat EE and potentially other inflammatory gastrointestinal diseases and conditions involving the esophagus. Although treatment with anti-IL-5 monoclonal antibody has been reported to be successful in EE, this therapy is currently not approved for use in children (36).

Current treatments include elimination diets (22, 23), and elemental formulas (2, 24). Identifying true inciting food allergens can be difficult and elemental formulas are often unpalatable, thereby making dietary interventions complicated (1, 22). Systemic corticosteroids and swallowed topical steroids, such as fluticasone proprionate (Flovent™) administered through metered-dose inhaler (MDI), have been shown to induce and maintain low esophageal eosinophil levels (25-30). In one method, for example, a fluticasone metered dose inhaler (MDI) is puffed into the oropharynx and swallowed (26). Improvised puff and swallow techniques may be difficult for patients, especially smaller children, and especially children with developmental delays, to perform efficiently. This may result in a less than effective dose of a topical steroid being delivered to the esophagus.

SUMMARY OF THE INVENTION

Provided herein are methods for preventing and alleviating any chronic inflammatory or malignant state that involves the esophagus and responds to steroid therapy. The methods of the present invention are useful, for example, for preventing and alleviating the symptoms and inflammation of eosinophilic esophagitis, inflammatory bowel diseases involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, Epidermolysis bullosa, and post-surgery inflammation. The present methods are also useful for preventing or alleviating symptoms and inflammation associated with other diseases or conditions of the gastrointestinal tract, for example, the upper gastrointestinal tract, where it is beneficial to target a particular target site, rather than provide systemic therapy. Also provided herein are pharmaceutical compositions useful in the methods of the present application.

Thus, in one embodiment is provided a method of preventing or alleviating esophageal inflammation in an individual comprising orally administering to said individual a corticosteroid in association with at least one excipient to increase the viscosity of the composition. In certain embodiments, the viscosity of the composition is about that of a suspension prepared by adding about 5 to about 15 grams of sucralose (Splenda®, Distributed By: McNeil Nutritionals, LLC, Fort Washington, Pa. 19034-2299) to 4 ml of water, or about 10 to about 12 grams of sucralose (Splenda®) to 4 ml of water, wherein the viscosity is measured at 25 degrees Celsius. In certain aspects, the corticosteroid is a topical corticosteroid, such as, for example, Budesonide. In some embodiments, the individual has eosinophilic esophagitis. The individual may, for example, have been diagnosed with a disease or condition selected from the group consisting of eosinophilic esophagitis, inflammatory bowel diseases involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, and post-surgery inflammation.

Although the methods of the invention may be used to prevent or alleviate esophageal inflammation in a mammal, for example a human, of any age, in certain examples, the individual is a child, for example, a child less than 16, 15, 14, 13, 12, 11, 10, 9, 8, 7, 6, 5, 4, 3, 2, or 1 years old.

Also provided in the present invention is a pharmaceutical composition comprising a corticosteroid and a viscosity-increasing excipient, for example, a topical corticosteroid, such as, for example, Budesonide. The pharmaceutical composition may be, for example, in liquid form. Also provided are pharmaceutical compositions comprising a corticosteroid, for example a topical corticosteroid, such as, for example, Budesonide, in the form of a dissolving tablet, a dissolving wafer, a capsule, or a gel capsule. In certain embodiments, these tablets, wafers, and capsules are formulated with at least one excipient to deliver a viscous form of the corticosteroid to the esophagus.

The excipient may be, for example, selected from the group consisting of lactose, sucrose, sucralose (Splenda®, Distributed By: McNeil Nutritionals, LLC, Fort Washington, Pa. 19034-2299), mannitol, sorbitol, honey, maize starch, wheat starch, rice starch, potato starch, gelatin, gum tragacanth, methyl cellulose, hydroxypropylmethyl-cellulose, sodium carboxymethyl-cellulose (CMC), and polyvinylpyrrolidone (PVP: povidone). The excipient may be, for example, selected from the group consisting of lactose, sucrose, sucralose (Splenda®), mannitol, sorbitol, honey, maize starch, wheat starch, rice starch, potato starch, gelatin, gum tragacanth, methyl cellulose, hydroxypropylmethyl-cellulose, sodium carboxymethyl-cellulose (CMC), and polyvinylpyrrolidone (PVP: povidone). In certain illustrative examples, the excipient is sucralose (Splenda®).

The pharmaceutical composition in certain embodiments comprises a therapeutically effective amount of corticosteroid to prevent or alleviate esophageal inflammation. In certain embodiments, 1-2 mg or 2-3 mg or corticosteroid per day is administered to said individual.

Provided in certain embodiments herein is a method of preventing or alleviating esophageal inflammation in an individual comprising orally administering to said individual a corticosteroid in association with at least one viscosity enhancing excipient, wherein upon oral administration, the corticosteroid is present in a medium with a viscosity of at least 2 cP at 25 degrees Celcius and a shear rate of about 13.2 $\sec^{-1}$.

In some embodiments, the pharmaceutical composition is in the form of a dissolvable tablet, a dissolvable wafer, or a dissolvable capsule. In some embodiments, the corticosteroid is administered in a pharmaceutical composition comprising the corticosteroid and the at least one viscosity enhancing excipient. In certain embodiments, the medium with a viscosity of at least 2 cP comprises the saliva of the individual, the corticosteroid and the at least one excipient.

In certain embodiments, the administered the pharmaceutical composition further comprises a liquid vehicle. In some embodiments, the pharmaceutical composition is a suspension comprising corticosteroid microparticles. In certain embodiments, the viscosity of the pharmaceutical composition is at least 10 cP at 25 degrees Celcius and a shear rate of about 13.2 $\sec^{-1}$.

In some embodiments, the pharmaceutical composition is administered once a day, twice a day, or three times a day. In certain embodiments, the pharmaceutical composition is administered no more than once a day.

In some embodiments, the corticosteroid is a topical corticosteroid. In specific embodiments, the corticosteroid is budesonide. In certain embodiments, the pharmaceutical composition comprises corticosteroid microparticles, wherein at least 95% of the corticosteroid microparticles have a diameter of less than 10 microns. In some embodiments, 0.5-10 mg corticosteroid per day is administered to said individual. In certain embodiments, oral administration of the pharmaceutical composition provides a decreased systemic load of corticosteroid, as measured by plasma $AUC_{0-\infty}$, when compared to inhaled administration delivering an identical amount of corticosteroid. In some embodiments, the viscosity enhancing excipient is selected from the group consisting of lactose, sucrose, sucralose, maltodextrin, dextrose, mannitol, sorbitol, honey, maize starch, wheat starch, rice starch, potato starch, gelatin, gum tragacanth, methyl cellulose, hydroxypropylmethyl-cellulose, a carboxymethyl cellulose (CMC), sodium carboxymethyl-cellulose (NaCMC), polyvinylpyrrolidone (PVP: povidone), and combinations thereof. In certain embodiments, the esophageal inflammation is eosinophilic esophagitis. In some embodiments, the esophageal inflammation is, and/or the individual has been diagnosed with, a disease or condition selected from, by way of non-limiting example, eosinophilic esophagitis, inflammatory bowel diseases involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, and post-surgery inflammation.

In some embodiments, provided herein is an oral pharmaceutical composition comprising a therapeutically effective amount of a corticosteroid, and a liquid vehicle, wherein the pharmaceutical composition has a viscosity of greater than 2 cP at 25° C. and a shear rate of about 13.2 $\sec^{-1}$, and wherein the pharmaceutical composition is suitable for oral administration. In certain embodiments, provided herein is a pharmaceutical composition has a viscosity about 50 cP or greater at 25° C. and a shear rate of about 13.2 $\sec^{-1}$. In specific embodiments, the pharmaceutical composition has a viscosity of about 200 cP at 25° C. and a shear rate of about 13.2 $\sec^{-1}$. In further or alternative embodiments, the oral pharmaceutical composition is thixatropic.

In certain embodiments, a pharmaceutical composition provided herein has a volume of about 2 mL to about 20 mL. In some embodiments, the corticosteroid present in a pharmaceutical composition provided herein is a topical corticosteroid. In specific embodiments, the topical corticosteroid is budesonide. In certain embodiments, a pharmaceutical composition described herein comprises about 250 µg to about 10 mg of corticosteroid. In some embodiments, an oral pharmaceutical composition provided herein comprises a viscosity enhancing agent. In some embodiments, the viscosity enhancing agent is selected from a crosslinked poly(acrylic acid), a carbomer homopolymer, a carbomer copolymer, acacia (gum arabic), agar, aluminum magnesium silicate, sodium alginate, sodium stearate, bladderwrack, bentonite, carbomer, carrageenan, Carbopol, a cellulose, ceratonia, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, polyethylene glycol, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose, a carboxymethyl-cellulose (CMC), silicon dioxide, polyvinylpyrrolidone (PVP: povidone) and combinations thereof.

In various embodiments, the pharmaceutical composition described herein are in the form of a suspension, solution, syrup, or slurry. In certain embodiments, provided herein are pharmaceutical compositions comprising corticosteroid microparticles, wherein at least 95% of the corticosteroid microparticles have a diameter of less than 10 microns.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
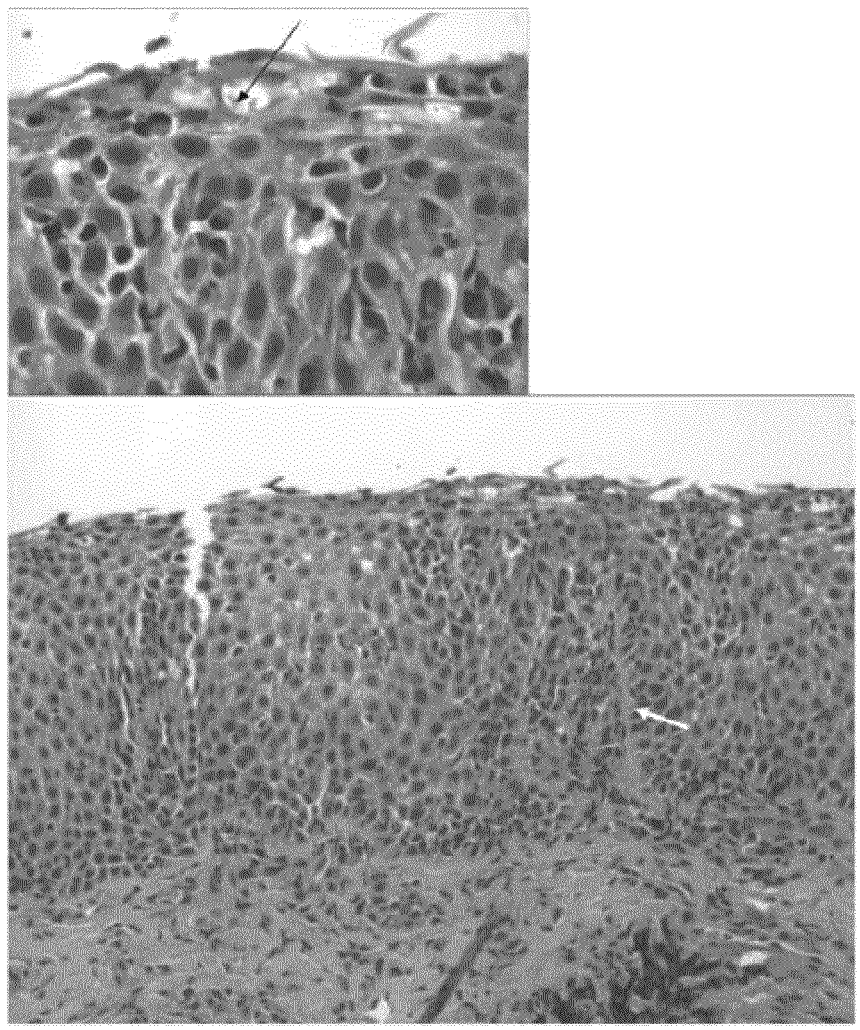
FIG. 1: Pretreatment distal esophageal biopsy showing marked basal zone hyperplasia (white arrow), numerous intraepithelial eosinophils (black arrow) with a few degranulated eosinophils, intercellular edema and fibrosis of the lamina propria (Hematoxylin & eosin, original magnification ×125; inset ×500). Basal zone hyperplasia is reported when basal zone cells extend towards the luminal surface of the epithelium (>25% of epithelial thickness).
Figure 2:
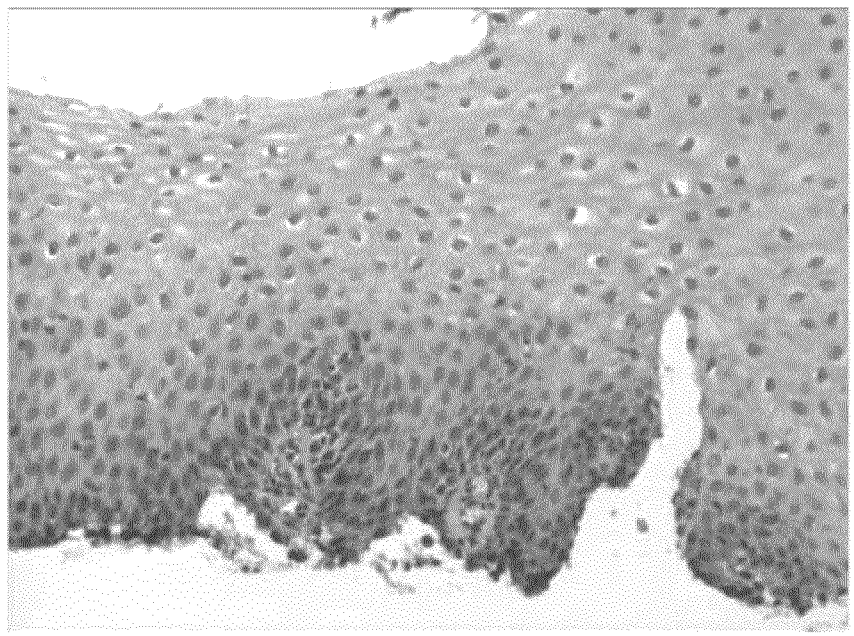
FIG. 2: Post-treatment distal esophageal biopsy showing normalization. Note absence of eosinophils and intercellular edema (Hematoxylin & eosin, original magnification ×125, inset ×500).
Figure 3:
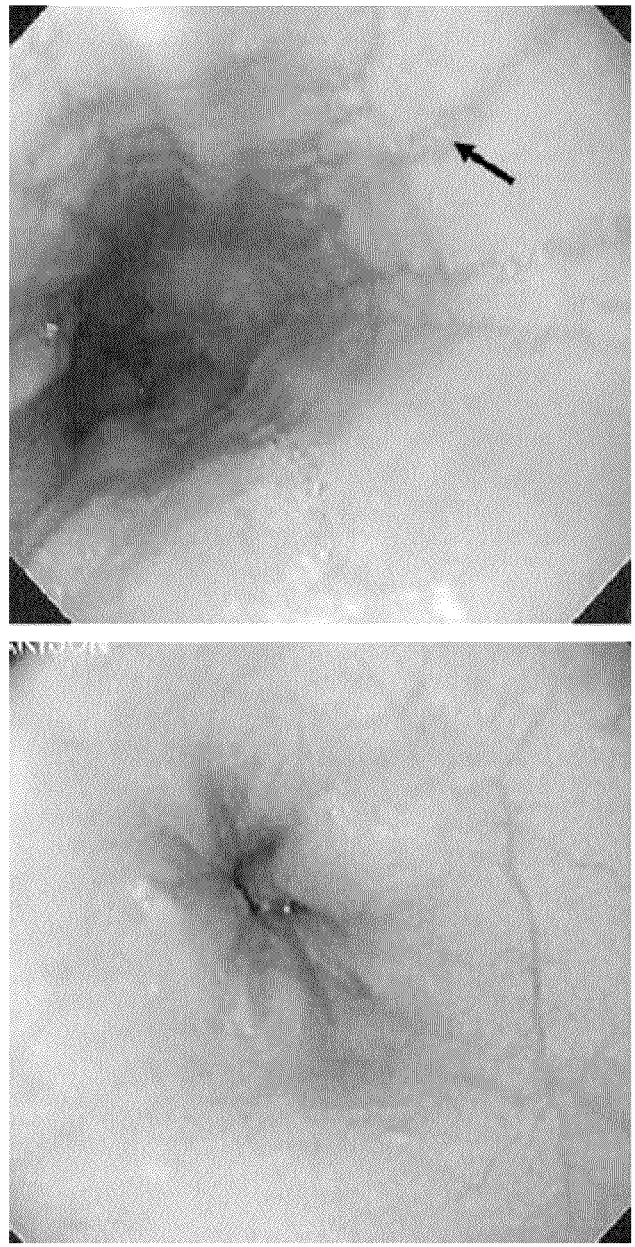
FIG. 3: Distal esophageal image of patient with eosinophilic esophagitis (Olympus P160 endoscope) showing pallor, lichenification of the mucosa with linear furrowing (arrow). Following treatment with viscous budesonide, the esophagus appears normal (lower).

Abbreviations: EE or EoE: Eosinophilic Esophagitis; MDI: Metered Dose Inhaler; hpf: high powered field; eos: eosinophil.

Provided herein are methods and pharmaceutical compositions for preventing or alleviating the symptoms of and inflammation associated with inflammatory diseases involving the esophagus.

In certain embodiments, the present invention is directed to methods and pharmaceutical compositions for treating, preventing or alleviating the symptoms of and inflammation associated with allergic or caustic inflammatory disorders involving the gastrointestinal tract, including the esophagus. Provided herein are methods of treating, preventing or alleviating, for example, esophageal inflammation in an individual. In certain embodiments, these methods comprise orally administering to said individual a corticosteroid. In some embodiments, provided herein is a method for treating, preventing or alleviating the symptoms of and inflammation associated with allergic or caustic inflammatory disorders involving the gastrointestinal tract, including the esophagus, by topically administering a corticosteroid to the gastrointestinal tract (e.g., esophagus). In specific embodiments, the corticosteroid is administered in a composition that coats a surface of the gastrointestinal tract (e.g., the esophagus). In some embodiments, the corticosteroid is administered along the length of (e.g., the entire length of) an afflicted surface of the gastrointestinal tract (e.g., the esophagus). In some embodiments, the corticosteroid is in a composition in association with at least one excipient to increase the ability of the composition to coat the surface of the gastrointestinal tract or a portion of the gastrointestinal tract (e.g., the esophagus). As used herein, in certain embodiments, an excipient that increases the ability of the composition to coat the surface of the gastrointestinal tract or portion thereof is used interchangeably with a coating agent. In certain instances, coating agents allow for an increased residence time of the composition on the surface of the gastrointestinal tract, or a portion thereof (e.g., esophagus). In some embodiments, the excipient that increases the ability of the composition to coat the gastrointestinal tract or portion thereof is an excipient that increases the viscosity of the composition (i.e., a viscosity enhancing agent). In some embodiments, provided herein is a pharmaceutical composition comprising a corticosteroid and a viscosity enhancing agent. In certain embodiments, a pharmaceutical composition described herein further comprises a liquid vehicle. In further or alternative embodiments, the pharmaceutical composition is suitable for oral administration. In some embodiments, the coating ability and/or increased viscosity of the composition allows the composition to be in contact with a surface of the gastrointestinal tract (e.g., the surface of the esophagus) for an extended period of time following administration. As used herein, coating agents are agents that increase the interaction of a composition or active within the composition with a surface of the gastrointestinal tract (e.g., the mucosa and/or epithelium of the gastrointestinal tract or of a specific site of the gastrointestinal tract, such as the esophagus).

An increase in the interaction of the composition with the surface of the gastrointestinal tract (e.g., esophagus) may be measured by measuring the retention time of the material along a length of a gastrointestinal surface, wherein the retention time is increased in the presence of the excipients as compared to its absence. As used herein, in certain embodiments, a gastrointestinal surface includes a gastrointestinal mucosa and/or a gastrointestinal epithelium, all of which terms are used interchangeably herein. In another embodiment, an increased interaction may be measured by the decrease in physiological manifestations or symptoms of the disease or ailment to be treated, including a decrease in total eosinophil counts in a sample collected from the surface tissue of the gastrointestinal tract (e.g., esophagus).

In some embodiments, provided herein is a viscous oral pharmaceutical composition comprising a corticosteroid. In certain embodiments, the viscous oral pharmaceutical composition comprises a viscosity sufficient to coat a targeted surface (e.g., an inflamed surface) of the gastrointestinal tract (e.g., the esophagus). In certain embodiments, the viscosity is any viscosity described herein, including, e.g., greater than about 50 cP at a shear rate of about 13.2 $sec^{-1}$.

In one aspect of the invention, the use of the excipients may act to decrease the quantity of active agents needed to elicit a response in the absence of the excipients. In some embodiments, the excipients may decrease the amount of corticosteroid used, for example, from about 1 to about 3 mg of budesonide in the absence of an excipient to about 250 µg to about 2 mg of budesonide in the presence thereof. Accordingly, the compositions provided herein may provide an additional advantage of decreasing the amount of active agent needed to treat subjects afflicted with allergic or caustic inflammatory diseases involving the gastrointestinal tract, including the esophagus.

It has been found that by administering Budesonide in oral form, in a formulation with increased fluid viscosity, that the corticosteroid was delivered to the esophagus in an effective dose to reduce the inflammation of the esophagus. In the treatment of more than 40 patients, this treatment was found to be effective in targeting inflammation within the esophagus. Specific examples of two patients, both children, are presented in Examples 1 and 2. A viscous oral suspension of budesonide improved symptoms, resolved endoscopic abnormalities, and markedly reduced or eliminated esophageal eosinophils in two patients unable to utilize a metered dose inhaler with puff and swallow technique. Although this therapy is particularly beneficial to children in that they often have the most difficulty using the puff and swallow technique, the methods of the present invention may also be used for individuals of any age. By "individual" is meant any animal, for example, a mammal, or, for example, a human, including, for example, patients in need of treatment.

Diseases

Provided herein are methods and pharmaceutical compositions for treating, preventing or alleviating the symptoms of, and inflammation associated with, caustic or allergic inflammatory disorders of the gastrointestinal tract, including but not limited to the upper gastrointestinal tract (e.g., the esophagus).

In certain embodiments, a corticosteroid (e.g., budesonide) that is administered in oral form, in a formulation with increased coating (e.g., viscosity and/or mucoadhesive) characteristic, is delivered to, e.g., the esophagus in an effective dose to reduce the inflammation of the esophagus.

Diseases or conditions that may be treated, prevented, or exhibit an alleviation of symptoms according to the present invention include any disease or condition that involves esophageal inflammation. This includes, for example, any chronic inflammatory or malignant state that involves the esophagus and responds to steroid therapy. The methods of the present invention are useful, for example, for preventing and alleviating the symptoms of eosinophilic esophagitis, inflammatory bowel diseases involving the esophagus, Crohn's disease, acute esophageal inflammation secondary to caustic/irritant ingestion, persistent/recurrent esophageal strictures secondary to caustic/irritant, conditions due to ingestion, systemic diseases, congenital diseases, and post-surgery inflammation.

An individual suitable for treatment with the compositions disclosed herein may, for example, have been diagnosed with a disease or condition including, but not limited to, eosinophilic esophagitis, inflammatory bowel diseases involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, or post-surgery inflammation. In some embodiments, the methods of treating, preventing or alleviating allergic or caustic inflammation, or symptoms thereof, include methods of treating any of the gastrointestinal disorders described herein. In certain embodiments, these methods comprise orally administering to said individual a corticosteroid-containing compositions described herein.

In certain embodiments, provided herein is a method of treating, preventing or alleviating allergic or caustic inflammation of the gastrointestinal tract, including, by way of non-limiting example, the esophagus, in an individual comprising orally administering to said individual any of the compositions described herein. In certain embodiments, the oral dosage form comprises a liquid vehicle and is formulated as, e.g., a slurry, suspension, syrup, dispersion, solution, etc.

In one aspect, a patient is administered a corticosteroid such as, for example, budesonide.

In some embodiments, the allergic or caustic inflammation treated by the methods and compositions described herein is associated with eosinophilic inflammation. In some embodiments, individuals (e.g., patients) to be treated with compositions described herein include those that have been diagnosed with eosinophilic esophagitis, an inflammatory bowel disease involving the esophagus, Crohn's disease, esophageal inflammation secondary to caustic/irritant ingestion, persistent/recurrent esophageal strictures of any cause and including caustic/irritant ingestion, pill-induced esophagitis, systemic diseases, congenital diseases, or post-surgery inflammation. In one non-limiting example, the patient has eosinophilic esophagitis. In some embodiments, the patient is an adult. In other embodiments, the patient is a child or infant. In other embodiments, the patient is a child or infant. In various aspects, a patient is a child or infant less than 19 years old, less than 16 years old, less than 12 years old, less than 8 years old, less than 6 years old, less than 4 years old, less than 2 years old, 2-18 years old, or 2-19 years old.

In some embodiments, a composition is in a unit dose formulation for oral administration to a patient. In some embodiments, a unit dose of the corticosteroid is administered from a metered dose device. In some embodiments, the metered dose device delivers a metered unit dose of a composition described herein to the mouth or throat of an individual in need thereof. In certain embodiments, the metered dose device is a metered inhaler, which is utilized to administer a metered unit dose to the mouth or throat of an individual (the individual swallows rather than inhales the metered unit dose). In some embodiments, a composition or unit dose described herein is administered as a nebulized composition, an aerosolized composition, an emulsion, a solution, a suspension, a syrup, a slurry, a dispersion, a colloid, a dissolving tablet, a dissolving wafer, a capsule, a gel capsule, a semi-solid, a solid form a gel, a gel matrix, a cream, a paste, or the like. In certain aspects, about 0.01 mg to about 20 mg, about 0.01 mg to about 15 mg, or about 0.01 mg to about 10 mg (e.g., about 0.1-10 mg, about 0.25-5 mg, about 0.25-2.5 mg, about 1-2 mg or about 2-3 mg, about 0.25 mg to about 6 mg corticosteroid, about 0.5 mg to about 6 mg corticosteroid, about 0.5 mg to about 2 mg of corticosteroid, about 1 mg to about 2 mg of corticosteroid, about 2 mg to about 3 mg of corticosteroid, about 3 mg to about 4 mg of corticosteroid, about 4 mg to about 5 mg of corticosteroid, or about 5 mg to about 6 mg of corticosteroid per day or per dose is administered to an individual. In some embodiments, the corticosteroid is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of corticosteroid administered daily or in a unit dose is between about 0.5 mg and about 3 mg. In other embodiments, the amount of corticosteroid present in a unit dose or administered daily is between about 1 and about 3 mg, or between about 1 and about 2 mg, or between about 2 and about 3 mg.

In certain aspects, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) corticosteroid per day is administered to a patient or individual. In some embodiments, the corticosteroid is present in a unit dose in an amount of between about 0.25 mg and about 5 mg. In some embodiments, the amount of corticosteroid administered daily or in a unit dose is between about 0.5 mg and about 3 mg. In other embodiments, the amount of corticosteroid present in a unit dose or administered daily is between about 1 and about 3 mg, or between about 1 and about 2 mg, or between about 2 and about 3 mg.

Provided in certain embodiments herein is a method of treating allergic or caustic inflammation of the gastrointestinal tract (e.g., of the esophagus) in an individual comprising coating an inflamed portion of the gastrointestinal tract (e.g., a portion or a substantial portion of the esophagus) of an individual with an effective amount of a pharmaceutical composition. In specific embodiments, the pharmaceutical composition comprising a therapeutically effective amount of a topically active corticosteroid. In certain embodiments, the pharmaceutical composition further comprises a coating agent (e.g., a mucoadhesive agent and/or a viscosity enhancing agent). In some embodiments, the inflamed portion of the gastrointestinal portion is at least partially coated, or substantially coated. In certain embodiments, the effective amount of the pharmaceutical composition is an amount sufficient to coat the esophagus (e.g., a volume as set forth herein). In certain embodiments, the allergic or caustic inflammation of the gastrointestinal tract is the esophagus and the composition at least partially coats the esophagus (including all or part of the inflamed portions of the esophagus). In specific embodiments, the inflammation of the gastrointestinal tract is allergic inflammation of the esophagus (e.g., eosinophilic esophagitis).

The present methods are also useful for treating, preventing or alleviating symptoms and/or allergic or caustic inflammation associated with other diseases or conditions of the gastrointestinal tract, for example, the upper gastrointestinal tract, where it is beneficial to target a particular target site, rather than provide systemic therapy. Also provided herein are pharmaceutical compositions useful in the methods of the present application. As used herein, caustic or allergic inflammation and/or symptoms associated with a disorder or disease disclosed herein includes inflammation and/or symptoms associated with, caused by and/or resulting from the disorder or disease.

In certain embodiments, provided herein is a method of treating allergic or caustic gastrointestinal inflammation in an individual comprising orally administering a pharmaceutical composition to an individual in need thereof and delivering the pharmaceutical composition to an inflamed portion of the gastrointestinal tract, wherein the pharmaceutical composition comprises a topically active corticosteroid. In further embodiments, upon delivery of the pharmaceutical composition to the inflamed portion of the gastrointestinal tract, the pharmaceutical composition coats the inflamed portion of the gastrointestinal tract. In further embodiments, coating of the inflamed portion of the gastrointestinal tract provides prolonged exposure of the inflamed portion of the gastrointestinal tract to the pharmaceutical composition. In still further embodiments, prolonged exposure of the inflamed portion of the gastrointestinal tract to the pharmaceutical composition provides increased local delivery of the corticosteroid. In some embodiments, increased local delivery of the corticosteroid to a surface of the gastrointestinal tract decreases undesired systemic absorption of the corticosteroid. In some embodiments, the inflamed portion of the gastrointestinal portion is at least partially coated, or substantially coated. In certain embodiments, the effective amount of the pharmaceutical composition is an amount sufficient to coat the esophagus (e.g., a volume as set forth herein). In certain embodiments, the allergic or caustic inflammation of the gastrointestinal tract is the esophagus and the composition at least partially coats the esophagus (including all or part of the inflamed portions of the esophagus). In specific embodiments, the inflammation of the gastrointestinal tract is allergic inflammation of the esophagus (e.g., eosinophilic esophagitis).

In some embodiments, provided herein is a method of reducing systemic exposure to a corticosteroid in an individual being treated for allergic or caustic gastrointestinal inflammation, the method comprising orally administering a pharmaceutical composition and coating an inflamed portion of the gastrointestinal tract with the pharmaceutical composition, wherein the pharmaceutical composition comprises a corticosteroid. In certain embodiments, systemic exposure to the corticosteroid is reduced by using a topical, locally acting corticosteroid, instead of a systemically acting corticosteroid for the treatment of allergic or caustic gastrointestinal inflammation. In some embodiments, the topical, local delivery of the pharmaceutical composition does not provide substantial systemic exposure. In some embodiments, the inflamed portion of the gastrointestinal portion is at least partially coated, or substantially coated with the pharmaceutical composition. In certain embodiments, the effective amount of the pharmaceutical composition is an amount sufficient to coat the esophagus (e.g., a volume as set forth herein). In certain embodiments, the allergic or caustic inflammation of the gastrointestinal tract is the esophagus and the composition at least partially coats the esophagus (including all or part of the inflamed portions of the esophagus). In specific embodiments, the inflammation of the gastrointestinal tract is allergic inflammation of the esophagus (e.g., eosinophilic esophagitis).

In certain embodiments, provided herein is a method of orally administering a composition comprising a corticosteroid wherein systemic exposure of corticosteroid is reduced (e.g., significantly reduced) compared to the pulmonary administration of a nebulized or aerosolized corticosteroid composition with the same nominal or delivered dose. In some embodiments, provided herein is a method of orally administering (e.g., by drinking or swallowing) a composition comprising a corticosteroid wherein systemic exposure of corticosteroid is reduced (e.g., significantly reduced) compared to the oral administration of a nebulized or aerosolized corticosteroid composition (which is sprayed on the targeted site of the gastrointestinal site, e.g., esophagus) comprising a corticosteroid.

It will be appreciated by those skilled in the art that reference herein to treatment extends to prophylaxis as well as the treatment of inflammation or other symptoms.

Compounds

In certain embodiments, the corticosteroids used in the present invention include topical steroids including, for example, budesonide. In some embodiments, corticosteroids are selected from, by way of non-limiting example, aclometasone, amcinomide, beclometasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluticasone, fluticasone propionate, fuprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, remexolone, tixocortol, triamcinolone and ulobetasol, and combinations, pharmaceutically acceptable salts and esters thereof. In a specific embodiment, the corticosteroid is budesonide.

In certain embodiments, the corticosteroid(s) utilized herein are utilized as particles (e.g., corticosteroid particles suspended or dispersed in an aqueous medium). In specific embodiments, the particles are microparticles. In some embodiments, the microparticles have a mean diameter of about 0.1 microns to about 50 microns. In specific embodiments, the microparticles have a mean diameter of about 1 micron to about 20 microns. In certain embodiments, at least 95%, at least 98%, or at least 99% of the microparticles have a diameter of less than 10 microns.

Formulation

While the compositions of the present invention will typically be used in therapy for human patients, they may also be used in veterinary medicine to treat similar or identical diseases. The compositions may, for example, be used to treat mammals, including, but not limited to, primates and domesticated mammals. The compositions may, for example be used to treat herbivores. The compositions of the present invention include geometric and optical isomers.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

Liquid suspensions of the present invention include, for example, those prepared by adding about 5 to about 25 grams of sucralose (Splenda®, Distributed By: McNeil Nutritionals, LLC, Fort Washington, Pa. 19034-2299), or about 7 to about 20 grams of sucralose (Splenda®), or about 5 to about 15 grams of sucralose (Splenda®), or about or about 7 to about 15 grams of sucralose (Splenda®), or about 8 to about 12 grams of sucralose (Splenda®), or about 10 to about 11 grams of sucralose (Splenda®), or 1, 2, 3, 4, 5, 6, 7, 8, 9, 10, 11, 12, 13, 14, 15, 16, 17, 18, 19, 20, 21, 22, 23, 24, or 25 grams of sucralose (Splenda®), added to 2 mL or 4 mL of Budesonide, such as that obtained from a Budesonide respule, or smaller or larger volumes having the same ratios of sucralose (Splenda®) to Budesonide. Smaller or larger volumes of formulations provided herein may also be used. In some embodiments, the volume used in a formulation provided herein comprises components in the ratios as described above.

The exact dosage will depend upon the route of administration, the form in which the composition is administered, the subject to be treated, the age, body weight/height of the subject to be treated, and the preference and experience of the attending physician. In certain embodiments, the optimal concentration of the corticosteroid in the composition depends upon the specific corticosteroid used, the characteristics of the patient, and the nature of the inflammation for which the treatment is sought. In various embodiments, these factors are determined by those of skill in the medical and pharmaceutical arts in view of the present disclosure.

Generally, a therapeutically effective dose is desired. A therapeutically effective dose refers to the amount of the corticosteroid that results in a degree of amelioration of symptoms and/or inflammation relative to the status of such symptoms and/or inflammation prior to treatment. The dosage forms and methods of applying dosage forms containing effective amounts are within the scope of the instant invention. In various embodiments, the amount of corticosteroid (e.g., budesonide) used in a method or in a composition described herein is from about 10 to 400 µg/kg of body weight per day, or for example, in the range of 20 to 300 µg/kg per day, or for example in the range of 30 to 200 µg/kg per day, or for example in the range of 30 to 100 µg/kg per day, or for example in the range of 35 to 100 µg/kg per day, or for example in the range of 10-50 µg/kg per day, or for example in the range of 10-100 µg/kg/day, or for example in the range of 30-50 µg/kg/day, in an illustrative embodiment in the range of 40-60 µg/kg/day, about 2.5 to 400 µg/kg of body weight per day, or for example, in the range of 5 to 300 µg/kg per day, or for example in the range of 5 to 200 µg/kg per day, or for example in the range of 5 to 100 µg/kg per day, or for example in the range of 10 to 100 µg/kg per day, or for example in the range of 5-50 µg/kg/day, or in an illustrative embodiment in the range of 10-60 µg/kg/day, or in an illustrative embodiment in the range of 30-60 µg/kg/day. In some embodiments, the amount of corticosteroid (e.g., budesonide) used in a method, in a composition or a dose of a composition disclosed herein includes, by way of non-limiting example, about 500 µg to about 2 mg, about 1 to about 2 mg, about 1 mg, about 2 mg, about 250 µg to about 20 mg, about 250 µg to about 15 mg, about 250 µg to about 10 mg, about 250 µg to about 5 mg, about 250 µg to about 3 mg, or about 500 µg to about 3 mg, about 375 µg to about 1.5 mg, or about 500 µg to about 2 mg, or about 1 mg to about 3 mg, about 0.25 mg, about 0.5 mg, about 1 mg, about 2 mg, about 2.5 mg, about 3 mg, about 4 mg, about 5 mg, or about 6 mg. In an illustrative embodiment, the dosage is provided in a sufficient volume that the composition reaches the esophagus in an effective amount.

In an illustrative embodiment, a dosage or amount (including a divided dose) of corticosteroid composition is in a volume that provides an effective amount of corticosteroid to the targeted and/or inflamed portion of the gastrointestinal tract, including, e.g., the esophagus. In some embodiments, the effective volume of the composition coats or at least partially coats the esophagus, and delivers the composition to the affected areas, including by way of example only, the lower esophagus, the upper esophagus, the esophagus, or a portion of the esophagus. In certain embodiments, a composition described herein has a volume of, for example about 5-50 mL, or for example about 5-40 mL, or for example about 5-30 mL, or for example about 5-25 mL, or for example about 10-25 mL, for example about 1-50 mL, or for example about 1-40 mL, or for example about 1-30 mL, or for example about 1-25 mL, or for example about 8-12 mL, or for example, about 7-8 mL, or for example, about 5-25 mL, or for example about 10-20 mL, or for example about 10 mL, or for example, about 15 mL, or for example, about 20 mL, or for example about 1-15 mL, or for example about 1-10 mL, or for example about 2-8 mL, or for example about 3-7 mL, or for example, about 4-6 mL, or for example, about 5 mL, or for example about 6-14 mL, or for example, about 4-15 mL, or for example, about 9-11 mL. In more specific embodiments, about 0.25 mg to about 6 mg, about 0.375 mg, about 0.5 mg, about 0.75 mg, about 1 mg, about 1.25 mg, about 1.5 mg, or about 2 mg of corticosteroid (e.g., budesonide) is formulated into a single or unit dose of a pharmaceutical composition described herein, the single or unit dose having a total volume of about 10-20 mL, or for example about 10 mL, or for example, about 15 mL, or for example, about 20 mL, or for example about 1-15 mL, or for example about 1-10 mL, or for example about 2-8 mL, or for example about 3-7 mL, or for example, about 4-6 mL, or for example, about 5 mL, or for example about 6-14 mL, or for example about 8-12, or for example, about 4-15 mL, or for example about 9-11 mL, or for example, about 10 mL.

As discussed herein, "liquid" encompasses slurries, solutions, suspensions, or any combination thereof, depending on the solubilities and amounts of the individual components and the vehicles and solvents used. In some embodiments, provided herein is a composition comprising a corticosteroid in a formulation used to treat a targeted portion of the gastrointestinal tract (e.g., the esophagus). In further embodiments the composition comprises (or is administered in) a volume used to coat a targeted portion of the gastrointestinal tract (e.g., the esophagus). In certain embodiments the volume used to coat a targeted portion of the gastrointestinal tract (e.g., the esophagus) is a volume that is sufficient to coat the targeted portion. In some embodiments, an appropriate palatable dosage is in a volume that coats or at least partially coats the esophagus, and in an illustrative embodiment, the volume coats or at least partially coats the esophagus and delivers the corticosteroid to the affected areas, including by way of example only, the esophagus, a portion of the esophagus, the upper esophagus, or the lower esophagus. In certain instances, the volume of a composition administered can provide a desired coating characteristic of a composition. As such, in some embodiments, provided herein is a composition comprising a corticosteroid, wherein the composition comprises (or is administered in) a volume sufficient to coat a targeted portion of the gastrointestinal tract (e.g., the esophagus). In certain embodiments, likewise, is provided herein a method of treating allergic or caustic inflammation of the gastrointestinal tract, or a symptom thereof, by administering to an individual in need thereof (e.g., one diagnosed with or suspected of suffering from eosinophilic esophagitis), a composition comprising a coriticosteroid and a liquid vehicle, wherein the composition has a volume sufficient to coat (or at least coat in a effective amount) of a targeted portion of the gastrointestinal tract (e.g. esophagus). In specific embodiments, a volume sufficient to coat the esophagus is a volume that provides a bolus when orally administered to an individual. In more specific embodiments, a volume sufficient to coat the esophagus is a volume that provides a bolus along the entire length of the esophagus (i.e., from immediately after passing the upper esophageal sphincter through the distal end of the esophagus, e.g., immediately prior to entering or passing the lower esophageal sphincter. Thus, in certain embodiments described herein, a coating volume is optionally utilized instead of or in addition to a coating agent described herein in order to coat the targeted portion of the gastrointestinal tract (e.g., esophagus), as described herein.

In certain embodiments, provided herein are methods of treating, preventing or alleviating the symptoms of and allergic or caustic inflammation associated with inflammatory disorders involving the gastrointestinal tract, including the esophagus by administering a corticosteroid to an individual in need thereof. In some embodiments, the corticosteroid is administered along the length of (e.g., the entire length of) an afflicted or targeted surface of the gastrointestinal tract (e.g., the esophagus). In some embodiments, the corticosteroid is administered in a composition that coats the afflicted or targeted surface of the gastrointestinal tract (e.g., esophagus). In some embodiments, administration of corticosteroid or a composition described herein is achieved by nebulization or aerosolization of the corticosteroid or composition followed by swallowing (and, thereby, administration to the esophagus). In certain embodiments, administration of a corticosteroid or a composition described herein is administered with a nebulizer or inhaler. In some embodiments, the inhaler administers a composition of a corticosteroid, a vehicle (e.g., a solid, liquid or gaseous, such as a propellant, vehicle). Specific methods include administration from a multi-dose inhaler (MDI) or dry powder inhaler (DPI). In some embodiments, coating volumes include any suitable amount, e.g., about 2 mL or more, about 3 mL to about 20 mL, about 4 mL to about 15 mL, about 5 mL or more, about 5 mL to about 20 mL, about 5 mL to about 15 mL, or about 5 mL to about 10 mL. In some embodiments, the powder delivered from the device (such as a DPI or MDI) alone is the composition which coats or is delivered along the length of the afflicted or targeted gastrointestinal surface (e.g., esophagus).

The dosage may, for example, be administered at least once a day, e.g., in four, three, two, or one dose a day. In one illustrative example, the dose is provided once a day. In specific embodiments, administration of any composition described herein (e.g., for the treatment of gastrointestinal or esophageal inflammation including eosinophilic esophagitis) is once a day. In other specific embodiments, administration (e.g., for the treatment of gastrointestinal or esophageal inflammation including eosinophilic esophagitis) is b.i.d. In still other embodiments, administration (e.g., for the treatment of gastrointestinal or esophageal inflammation including eosinophilic esophagitis) is t.i.d. In yet other embodiments, administration (e.g., for the treatment of gastrointestinal or esophageal inflammation including eosinophilic esophagitis) is q.i.d. In another embodiment, the dose is administered at night. In another aspect, the dose is administered about 30 minutes prior to bed, with no food or water given after administration of the compositions herein. In yet another embodiment of the instant invention, the dose is administered prior to bedtime, wherein after administration of the composition, the patient or individual is in a substantially supine position for at least 30 minutes, at least 1 hour, at least 2 hours, at least 4 hours, at least 8 hours, about 30 minutes to about 8 hours, about 30 minutes to about 4 hours, about 1 hour to about 8 hours, or, about 1 hour to about 6 hours. In some embodiments provided herein, the dose is administered prior the individual being in a substantially supine position for at least 30 minutes, at least 1 hour, at least 2 hours, at least 4 hours, at least 8 hours, about 30 minutes to about 8 hours, about 30 minutes to about 4 hours, about 1 hour to about 8 hours, or, about 1 hour to about 6 hours. In specific embodiments, a corticosteroid or composition is administered according to any method described herein, wherein administration of the corticosteroid or composition is once a day, no more than once a day, more than once a day, twice a day, two to four times a day, three times a day, or four times a day. In some embodiments, the administration of the corticosteroid or composition provided herein is administered at night, e.g., not more than once a day at night.

In some embodiments, the corticosteroid is present in a pharmaceutical composition described herein in any effective amount. In some embodiments, an effective amount is an amount sufficient to reduce inflammation or symptoms of inflammation associated with an allergic or caustic inflammatory disorder or condition of the gastrointestinal tract (e.g., the esophagus) as compared to the level of inflammation or symptoms of inflammation associated with an allergic or caustic inflammatory disorder prior to administration of the effective amount. In certain embodiments, effective amount is an amount sufficient to maintain a reduction in inflammation or symptoms of inflammation achieved in any manner including, but not limited to, by the administration of an effective amount sufficient to achieve such a reduction. In some embodiments, the effective amount is about 0.5 mg to about 2 mg, about 1 mg to about 2 mg, about 1 mg, or about 2 mg of corticosteroid. In certain embodiments, the corticosteroid is present in a pharmaceutical composition at any concentration suitable for providing a therapeutically effective amount of corticosteroid to a surface of the gastrointestinal tract (e.g., the surface of the esophagus), e.g., about 0.06 mg/mL to about 0.13 mg/mL. In some embodiments, the concentration of corticosteroid present in the pharmaceutical composition is about 0.01 mg/mL to about 2 mg/mL of composition. In specific embodiments, the corticosteroid is present in a pharmaceutical composition at a concentration of about 0.01 mg/mL to about 1.5 mg/mL, about 0.03 mg/mL to about 1.5 mg/mL, about 0.05 mg/mL to about 1.5 mg/mL, about 0.07 mg/mL to about 1.5 mg/mL, about 0.05 mg/mL to about 0.2 mg/mL, or about 0.06 mg/mL to about 0.13 mg/mL. In more specific embodiments, the corticosteroid is present in a pharmaceutical composition at a concentration of about 0.07 mg/mL to about 1 mg/mL. In more specific embodiments, the corticosteroid is present in a pharmaceutical composition at a concentration of about 0.07 mg/mL to about 1 mg/mL. In some embodiments, any composition described herein comprises an amount or concentration of corticosteroid sufficient to provide about 0.5 mg to about 6 mg of corticosteroid per day, about 0.05 mg to about 10 mg, about 0.05 mg to about 7.5 mg, about 0.05 mg to about 5 mg, about 0.25 mg to about 3 mg, about 0.25 mg to about 2.5 mg, about 0.5 mg to about 3 mg, about 0.5 mg to about 2 mg, about 0.5 mg to about 0.1 mg, about 0.5 mg to about 5 mg, about 0.5 mg to about 4 mg, about 1 mg to about 4 mg, about 1 mg to about 3 mg, about 2 mg to about 3 mg, or about 2 mg to about 4 mg. In certain embodiments, the effective amount of corticosteroid (per dose or per day) is about 0.05 mg, about 0.1 mg., about 0.15 mg., about 0.25 mg., about 0.3 mg., about 0.35 mg, about 0.4 mg, about 0.37 mg, about 0.375 mg, about 0.7 mg, about 0.8 mg, about 0.75 mg, about 1 mg, about 1.2 mg, about 1.25 mg, about 1.3 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 6 mg or more, about 1 mg to about 6 mg, about 0.25 mg to about 6 mg, or about 7.5 mg or more. In some embodiments, the effective amount of corticosteroid is about 0.5 mg to about 2 mg of corticosteroid per day, about 1 mg to about 2 mg of corticosteroid per day, about 2 mg to about 3 mg of corticosteroid per day, about 3 mg to about 4 mg of corticosteroid per day, about 4 mg to about 5 mg of corticosteroid per day, or about 5 mg to about 6 mg of corticosteroid per day. In certain embodiments, provided herein is a method of treating allergic or caustic inflammation of the gastrointestinal tract or a symptom thereof by administering a sufficient amount of a composition described herein to provide about 0.5 mg to about 6 mg of corticosteroid per day, about 0.5 mg to about 2 mg of corticosteroid per day, about 1 mg to about 2 mg of corticosteroid per day, about 2 mg to about 3 mg of corticosteroid per day, about 3 mg to about 4 mg of corticosteroid per day, about 4 mg to about 5 mg of corticosteroid per day, or about 5 mg to about 6 mg of corticosteroid per day to an individual in need thereof.

In specific embodiments, the composition described herein is a composition comprising a corticosteroid, dextrose, maltodextrin, polysorbate (e.g., polysorbate 80), an optional sweetener and a liquid vehicle. In some specific embodiments, the composition described herein is a composition comprising a corticosteroid, maltodextrin and a liquid vehicle. In certain specific embodiments, the composition described herein is a composition comprising a corticosteroid, dextrose and a liquid vehicle. In some specific embodiments, the composition described herein is a composition comprising a corticosteroid and maltodextrin. In some specific embodiments, the composition described herein is a composition comprising a corticosteroid and dextrose.

In other illustrative embodiments of the invention, the Budesonide is provided in the form of a lozenge which may be dissolved in the mouth, thus reaching and coating the esophagus. The lozenge or other similar tablet, capsule, or other solid, would dissolve rapidly in the mouth or esophagus to produce a solution that can then coat the esophagus. Or, for children or other patients that may have difficulty with a dissolving lozenge, the lozenge may be ground or otherwise dissolved in a small volume of water or other pharmaceutically suitable liquid, for example, reaching a total volume presented in embodiments herein. In other illustrative embodiments of the invention, the Budesonide is provided in the form of a tablet, a capsule, or, for example a gel capsule, designed for slow release and delivery to the esophagus.

Initial treatment may continue, for example, for about 3 days to 2 weeks for an acute condition, or about 4 weeks to about 16 weeks for a chronic condition, or about 8 weeks to about 12 weeks for a chronic condition. Longer therapy may also be needed, such as, for example, therapy similar to chronic therapy for persistent asthma. Patients may, for example, be treated for up to 6 months, or up to one year. Maintenance treatment can last up to or longer than one year. Patients may be treated on a maintenance basis or on an as needed basis during a problematic episode, depending on the severity of the condition. Patients can also be treated on a rotating treatment basis, where treatment is provided for a period of time and then the patient is taken off of the drug for a period before treatment resumes again. When off the drug, the patient may be given no treatment, treatment with another medication, or treatment with a reduced dosage. Or, patients may be given treatment with a higher dose of the composition until a desired reduced disease state is achieved, and then continued on a lower dose of the composition.

The methods and compositions of the present invention are used by individuals of any age. By "individual" is meant any animal, for example, a mammal, or, for example, a human, including, for example, patients in need of treatment. In some embodiments, the human is a child.

The compositions of the present invention may include pharmaceutically acceptable salts. Pharmaceutically acceptable salts are generally well known to those of ordinary skill in the art and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In one aspect, provided herein is an oral pharmaceutical composition comprising a corticosteroid and a coating agent (e.g., a viscosity enhancing agent and/or a mucoadhesive agent). In various aspects, an exemplary corticosteroid is budesonide, 16,17-(butylidenebis(oxy))-11,21-dihydroxy-, (11-β,16-α)-pregna-1,4-diene-3,20-dione.

Depending on the specific conditions being treated, the compositions may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000).

In certain embodiments, the pharmaceutical compositions provided herein are used to treat, prevent or alleviate allergic or caustic inflammatory disorders involving the gastrointestinal tract, including the esophagus. In some embodiments, the pharmaceutical composition is in liquid form. Liquid forms include, by way of non-limiting example, solutions, suspensions, syrups, slurries, dispersions, colloids, —and the like. Also provided are pharmaceutical compositions comprising a corticosteroid (e.g., a topical corticosteroid, such as, for example, budesonide) and a coating agent (e.g., a viscosity-increasing excipient) in the form of a dissolving tablet, a dissolving wafer, a capsule, or a gel capsule. In some embodiments, a pharmaceutical composition described herein is in liquid, semi-solid or solid form. In specific embodiments, a pharmaceutical composition described herein is in semi-solid form, e.g., a gel, a gel matrix, a cream, a paste, or the like. In some embodiments, semi-solid forms comprise a liquid vehicle. In some embodiments, the solid form is a solid dosage form, such a tablet, or a powder. In certain embodiments, solid dosage forms described herein comprise a solid vehicle (e.g., as used in a tablet), and/or a gaseous vehicle (e.g., as used in DPI).

In addition to the active or actives, various embodiments of the present invention provide for pharmaceutical compositions that contain suitable pharmaceutically acceptable excipients and auxiliaries. For example, in some embodiments, pharmaceutically acceptable excipients and/or auxiliaries are used to formulate the corticosteroids herein disclosed for the practice of the invention into dosages suitable for systemic administration is within the scope of the invention. In some embodiments, the corticosteroid is formulated readily using pharmaceutically acceptable excipients and/or auxiliaries well known in the art into dosages suitable for oral administration. Such excipients and/or auxiliaries enable the compositions of the invention to be formulated as tablets, pills, dragees, capsules, liquids, soft chews, creams, pastes, chewable tablets, gels or gel matrices, gums, syrups, slurries, suspensions, lozenges, and the like, for oral ingestion by a patient to be treated. In certain instances, oral formulations (e.g., suspensions, creams or gel matrices) are formulated such that upon oral administration, an interface layer between the oral formulation (e.g., suspension, cream or gel matrix) and a gastrointestinal surface (e.g., mucosal membrane or epithelium) is formed. In some instances, an oral formulation (e.g., suspensions, creams or gel matrices) in contact with a gastrointestinal surface (e.g., mucosal membrane or epithelium) delivers a corticosteroid to the gastrointestinal surface (e.g., mucosal membrane or epithelium) via the interface layer and as the oral formulations (e.g., suspensions, creams or gel matrices) near the interface layer is depleted of corticosteroid, a concentration gradient results. In certain instances an osmotic delivery of corticosteroid may occur. In some instances, portions of the oral formulations (e.g., suspensions, creams or gel matrices) with high concentrations of corticosteroid, relative to the portions of the oral formulations (e.g., suspensions, creams or gel matrices) proximate to the interface layer, replenishes corticosteroid in the portion of the oral formulations (e.g., suspensions, creams or gel matrices) proximate to the interface layer. In certain instances, upon oral administration of an oral formulation described herein to an individual, an interface layer is formed between a gastrointestinal surface (e.g., mucosal membrane or epithelium) and a mixture of the oral formulation (e.g., lozenge or dissolving or chewable tablet) and saliva of the individual.

Pharmaceutical preparations for oral use may be obtained by combining the corticosteroids with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, sucralose (Splenda®, Distributed By: McNeil Nutritionals, LLC, Fort Washington, Pa. 19034-2299), mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate. For dissolving tablets, appropriate excipients include those that increase the resulting liquid viscosity of the dissolved tablet, enabling it to reach the esophagus, for example, to coat the esophagus. Appropriate excipients may also, for example, include those that render the dissolving tablet palatable, such as sweeteners.

For liquid form, appropriate excipients may be added to increase the coating ability and/or liquid viscosity of the liquid composition. Appropriate excipients may also, for example, include those that render the liquid composition palatable. Excipients may include, for example, either sugars, including lactose, sucrose, sucralose (Splenda®, Distributed By: McNeil Nutritionals, LLC, Fort Washington, Pa. 19034-2299), maltodextrin, dextrose, mannitol, or sorbitol; honey; cellulose preparations, for example, maize starch, wheat starch, rice starch, potato starch, gelatin, gum tragacanth, methyl cellulose, hydroxypropylmethyl-cellulose, carboxymethyl-cellulose (CMC) (e.g., sodium carboxymethyl-cellulose (NaCMC)), and/or polyvinylpyrrolidone (PVP: povidone).

Viscosity-enhancing excipients that are useful in pharmaceutical compositions described herein include, but are not limited to, acacia (gum arabic), agar, aluminum magnesium silicate, sodium alginate, sodium stearate, bladderwrack, bentonite, carbomer, carrageenan, Carbopol, cellulose, a viscosity enhancing derivative of cellulose, ceratonia, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), carboxymethyl-cellulose (CMC), e.g., sodium carboxymethyl-cellulose (NaCMC), silicon dioxide, polyvinylpyrrolidone (PVP: povidone), Splenda®, or combinations thereof. In one non-limiting example, the viscosity-enhancing excipient is Splenda®. In a specific embodiment, the viscosity enhancing agent is selected from, by way of non-limiting example, Carbopol 974P, Carbopol Ultrez 10, sodium alginate LF120 and sodium alginate H120L. In some embodiments, the viscosity enhancing agent is selected from, by way of non-limiting example, PVP 10,000, PEG 3350 and HiFibro. In specific embodiments, the viscosity enhancing agent used in any composition described herein is or comprises maltodextrin.

In some embodiments, a composition or formulation described herein comprises a viscosity enhancing agent that imparts on the composition a viscosity sufficient to provide increased residence on the esophagus while also allowing migration of the active agent(s) (solute or particles) when the composition is orally administered to an individual. In other words, in some embodiments, the viscosity is high enough to increase residence time of the composition on a gastrointestinal surface (e.g., an epithelial layer and/or mucosal membrane), but not so high as to prevent migration of the active agent(s) within the composition, e.g., toward the gastrointestinal surface (e.g., an epithelial layer and/or mucosal membrane).

In certain embodiments, a pharmaceutical composition described herein is a non-newtonian fluid. In some specific embodiments, the non-newtonian fluid is thixotropic. In certain embodiments, the non-newtonian fluid composition thins with shear, and thickens upon the absence of shear. In some embodiments, the at least one additional excipient is selected from a non-newtonian viscosity enhancing agent (i.e., an agent that provides a composition herein with a non-newtonian character). Non-newtonian viscosity enhancing agents include, by way of non-limiting example, acacia (e.g., used in about 5-10% w/w of a pharmaceutical composition described herein), alginic acid (e.g., about 0.5-20% w/w), carbomer, CaCMC, NaCMC, carrageenan (e.g., about 0.3-12% w/w), ceratonia (e.g., about 0.1-1% w/w), chitosin (e.g., about 0.5-2% w/w), colloidal silicon dioxide (e.g., about 2-10% w/w), ethylcellulose (e.g., about 5-25% w/w), gelatin, guar gum (e.g., about 1-2.5% w/w), HEC, hydroxyethylmethyl cellulose (e.g., about 1-5% w/w), hydroxypropyl cellulose (e.g., about 1-10% w/w), HPMC, magnesium aluminum silicate (e.g., about 2-10% w/w), one or more maltodextrin, methylcellulose (e.g., about 1-2% w/w), polyethylene glycol (e.g., about 45-60% w/w), povidone (e.g., about 10-15% w/w), saponite, sodium alginate (e.g., about 1-5% w/w), sucrose (e.g., about 50-70% w/w), tragacanth (e.g., about 0.1-2% w/w), xanthan gum (e.g., about 0.1-1% w/w), an combinations thereof.

In certain embodiments, pharmaceutical compositions disclosed herein and used herein comprise one or more additional excipients. Excipients useful herein include, by way of non-limiting example, mucoadhesive agents, viscosity enhancing agents, binders, fillers, lubricants, solvents, flavoring agents, sweeteners, antioxidants, buffering agents, surfactants, —and the like.

Mucoadhesive agents to be used herein include, by way of non-limiting example, a soluble polyvinylpyrrolidone polymer (PVP), a carbopol, a crosslinked poly(acrylic acid) (e.g., Carbopol 974P), a carbomer homopolymer, a carbomer copolymer, a water-swellable, but water-insoluble, fibrous, cross-linked carboxy-functional polymer, a hydrophilic polysaccharide gum, one or more maltodextrin, alginate, a cross-linked aliginate gum gel, thiomers (e.g., thiolated chitosan, thiolated polycarbophil, thiolated alginate, thiolated cellulose derivatives, thiolated carboxymethyl cellulose, thiolated polyacrylic acid, or thiolated polyacrylates), PEGylated polymers (e.g., PEGylated polyacrylic acid or PEGylated polyacrylates), lectin, hydroxypropyl methyl cellulose (HPMC), cellulose derivatives, HPMA copolymers, a water-dispersible polycarboxylated vinyl polymer. In some embodiments, the mucoadhesive agent is a carbopol. In some embodiments, a mucoadhesive agent utilized in an oral pharmaceutical composition described herein imparts an increased viscosity upon the oral pharmaceutical composition (e.g., compared to an otherwise identical composition lacking the mucoadhesive agent).

In some embodiments, mucoadhesive agents that may be used in certain embodiments of the compositions and methods described herein are described, for example, in U.S. Pat. Nos. 6,638,521, 6,562,363, 6,509,028, 6,348,502, 6,306,789, 5,814,330, and 4,900,552, each of which is hereby incorporated by reference in its entirety.

In one non-limiting example, a mucoadhesive agent can be, by way of non-limiting example, at least one or at least two particulate components selected from titanium dioxide, silicon dioxide, and clay. In some embodiments, when the composition is not further diluted with any liquid prior to administration, the level of silicon dioxide is from about 3% to about 15%, by weight of the composition. In certain embodiments, silicon dioxide is selected from, by way of non-limiting example, fumed silicon dioxide, precipitated silicon dioxide, coacervated silicon dioxide, gel silicon dioxide, and mixtures thereof. In some embodiments, clay is selected from, by way of non-limiting example, kaolin minerals, serpentine minerals, smectites, illite or mixtures thereof. In certain embodiments, clay is selected from, by way of non-limiting example, laponite, bentonite, hectorite, saponite, montmorillonites or mixtures thereof.

In some embodiments, compositions described herein comprise maltodextrin. In some embodiments, compositions described herein comprise about 0.05 g of maltodextrin per mL of liquid vehicle to about 0.6 g of maltodextrin per mL of liquid vehicle. In certain embodiments, compositions described herein comprise about 0.1 g of maltodextrin per mL of liquid vehicle to about 0.6 g of maltodextrin per mL of liquid vehicle. In certain embodiments, compositions described herein comprise about 0.2 g of maltodextrin per mL of liquid vehicle to about 0.5 g of maltodextrin per mL of liquid vehicle. In some embodiments, compositions described herein comprise about 0.1 g of maltodextrin per mL of liquid vehicle to about 0.4 g of maltodextrin per mL of liquid vehicle. In certain embodiments, compositions described herein comprise about 0.2 g of maltodextrin per mL of liquid vehicle to about 0.4 g of maltodextrin per mL of liquid vehicle. In some embodiments, compositions described herein comprise about 0.2 g of maltodextrin per mL of liquid vehicle to about 0.3 g of maltodextrin per mL of liquid vehicle. In certain embodiments, compositions described herein comprise about 0.25 g of maltodextrin per mL of liquid vehicle to about 0.28 g of maltodextrin per mL of liquid vehicle. In some embodiments, compositions described herein comprise about 0.1 g of maltodextrin per mL of liquid vehicle, about 0.15 g of maltodextrin per mL of liquid vehicle, about 0.2 g of maltodextrin per mL of liquid vehicle, about 0.25 g of maltodextrin per mL of liquid vehicle, about 0.3 g of maltodextrin per mL of liquid vehicle, about 0.35 g of maltodextrin per mL of liquid vehicle, about 0.4 g of maltodextrin per mL of liquid vehicle, about 0.45 g of maltodextrin per mL of liquid vehicle, about 0.5 g of maltodextrin per mL of liquid vehicle, about 0.55 g of maltodextrin per mL of liquid vehicle, or about 0.6 g of maltodextrin per mL of liquid vehicle.

Any of the compositions or formulations described herein optionally comprise one or more agent for increasing the mucoadhesive character of a composition, optionally comprise one or more binder, one or more filler, optionally comprise one or more lubricant, optionally comprise one or more solvent, optionally comprise one or more sweetener, optionally comprise one or more antioxidant, optionally comprise one or more buffering agent, optionally comprise one or more surfactant, or combinations thereof.

Buffering agents include, by way of non-limiting example, citrate buffers (i.e., citric acid and citrate), phosphate buffers, acetate buffers, combinations thereof, or the like.

As used herein, "citrate" includes all compounds of Formula I wherein each R is independently selected from an H and a negative charge (e.g., as a salt or as a disassociated salt or acid). In certain embodiments, citrate is selected from, by way of non-limiting example, sodium citrate, citric acid and the like.

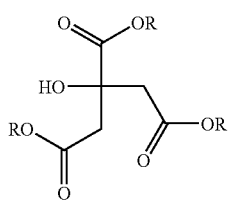

Formula I

Antioxidants include, by way of non-limiting example, ascorbyl palmitate, butylated hydroxyanisole, butylated hydroxytoluene, monothioglycerol, sodium ascorbate, sodium formaldehyde sulfoxylate, sodium metabisulfite, BHT, BHA, sodium bisulfite, vitamin E or a derivative thereof, propyl gallate, combinations thereof, or the like. Compositions and formulations described herein optionally include of about 0.01% w/w to about 0.5% w/w, about 0.01% w/w to about 0.3% w/w, or about 0.01% w/w to about 0.1% w/w one or more antioxidant(s).

In some embodiments, antioxidants include, by way of non-limiting example, edetate (EDTA) (e.g., disodium edetate), Diethylenetriaminepentaacetic acid (DTPA), Triglycollamate (NT), or the like. Compositions and formulations described herein optionally include about 0.01% w/w to about 0.5% w/w, about 0.01% w/w to about 0.3% w/w, or about 0.01% w/w to about 0.1% w/w, or about 0.05% w/w of edetate (or salt thereof).

As used herein, "edetate" includes all compounds of Formula II wherein each R is independently selected from an H and a negative charge (e.g., as a salt or as a disassociated salt or acid). In certain embodiments, edetate is selected from, by way of non-limiting example, disodium edetate, calcium edetate, ethylenediaminetetraacetic acid and the like.

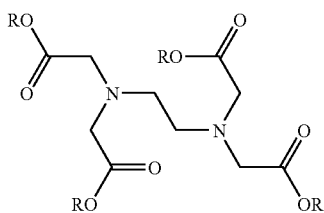

Formula II

In certain embodiments, sweeteners include, by way of non-limiting example, glycerin, sucrose, lactose, glucose, fructose, arabinose, xylose, ribose, mannose, galactose, dextrose, sorbose, sorbitol, mannitol, maltose, cellobiose, xylitol and the like.

Surfactants include, e.g., anionic, cationic, non-ionic, or zwitterionic surfactants, such as, by way of non-limiting example, polysorbate (e.g., polysorbate 20, polysorbate 60, polysorbate 40, polysorbate 80, polysorbate 81, polysorbate 85, polysorbate 120), bile acids or their salts (e.g., sodium taurocholates, sodium deoxytaurocholates, chenodeoxycholic acid, and ursodeoxycholic acid), nonoxynol or polyoxyethylene glycol fatty acid esters, pluronic or poloxamers such as Pluronic F68, Pluronic L44, Pluronic L101, combinations thereof, or the like. Compositions and formulations described herein optionally include about 0.001% w/w to about 0.5% w/w, about 0.001% w/w to about 0.3% w/w, or about 0.001% w/w to about 0.1% w/w of one or more surfactant.

In certain embodiments, a corticosteroid (e.g., budesonide) that is administered in oral form, in a formulation with increased fluid viscosity (including a formulation having increased viscosity when a composition described herein is contacted with saliva), is delivered to, e.g., the esophagus in an effective dose to reduce the inflammation of the esophagus.

As discussed above, in some embodiments, the liquid viscosity is increased in the oral form. In some embodiments, however, the excipient increases the viscosity of the dissolved form of a solid dosage form, such as a tablet. In certain embodiments, the viscosity is at a level that is sufficient to deliver an effective amount of the composition to the esophagus, for example, in an amount that allows for the coating of the esophagus. In some embodiments, the viscosity is at a level that when given orally is not so thick that it is too difficult to swallow, causes gagging, or is unpalatable. One method of determining whether the composition is sufficiently viscous is by determining whether the inflammation, or eosinophilic infiltration, of the esophagus is reduced after treatment with the corticosteroid.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active corticosteroid doses.

Pharmaceutical preparations that may be used orally also include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the corticosteroids may be dissolved or suspended in suitable liquids, such as fatty oils, liquid paraffin, or liquid polyethylene glycols (PEGs). In addition, stabilizers may be added.

In some embodiments, the corticosteroid is administered in a composition comprising a commercially available formulation of a corticosteroid. For example, in some embodiments, the corticosteroid containing composition comprises a commercially available formulation and an excipient, such as an excipient that imparts a mucoadhesive characteristic to the composition and/or a diluent. In some embodiments, wherein the corticosteroid is budesonide, the commercially available formulation is Pulmicort Respules®. In certain embodiments, a composition provided herein comprises (1) commercially available micronized corticosteroid particles (e.g., micronized budesonide), or other commercially available corticosteroid particles; and (2) a diluent or vehicle (e.g., an aqueous liquid vehicle) to provide a composition as described herein (e.g., one having a volume sufficient to coat the esophagus). In some embodiments, a composition provided herein comprises (1) commercially available micronized corticosteroid particles (e.g., micronized budesonide), or other commercially available corticosteroid particles; (2) an excipient that increases the interaction of the composition and/or corticosteroid with a surface of the gastrointestinal tract (e.g., esophagus); and (3) optionally a diluent or vehicle (e.g., an aqueous liquid vehicle) to provide a composition as described herein (e.g., one having a volume sufficient to coat the esophagus). In specific embodiments, the commercially available micronized corticosteroid particles are provided in a suspension, e.g., a commercially available suspension such as Pulmicort Respules®. In certain embodiments, provided herein is a method of preparing such a composition by combining each of the components and mixing them together.

In certain embodiments, the corticosteroid containing composition comprises micronized budesonide, disodium edetate, sodium chloride, sodium citrate, citric acid, polysorbate (e.g., polysorbate 80), water, and optionally one or more excipients, wherein the excipients are selected from any of those recited herein. In certain embodiments, the composition comprises about 0.1 mg to about 1.0 mg budesonide/2 mL (or about 0.05 mg to about 0.5 mg per gram) of composition. In some embodiments, the composition comprises about 0.2 mg to about 0.6 mg budesonide/2 mL (or about 0.1 mg to about 0.3 mg per gram) of composition. In specific embodiments, the composition comprises about 0.25 mg/2 mL composition. In other specific embodiments, the composition comprises about 0.5 mg/2 mL composition.

In one illustrative embodiment, the corticosteroid of the composition has a low bioavailability, so that much of it will remain in the gastrointestinal tract, for example, in the esophagus. This may result in decreased systemic side effects and complications, allowing patients with chronic conditions to receive treatment for longer periods of time. In certain embodiments, provided herein is a method of orally administering a composition comprising a corticosteroid wherein systemic exposure of corticosteroid is reduced (e.g., significantly reduced) compared to the pulmonary administration of a nebulized or aerosolized corticosteroid composition with the same nominal or delivered dose. In some embodiments, provided herein is a method of orally administering (e.g., by drinking or swallowing) a composition comprising a corticosteroid wherein systemic exposure of corticosteroid is reduced (e.g., significantly reduced) compared to the oral administration of a nebulized or aerosolized corticosteroid composition (which is sprayed on the targeted site of the gastrointestinal site, e.g., esophagus) comprising a corticosteroid. In some embodiments, the area under the curve ($AUC_{0-\infty}$) for the plasma concentration of an orally administered corticosteroid composition described herein to the gastrointestinal tract according to any methods described herein is less than 90%, less than 80%, less than 70%, less than 60%, between 50% and 90%, between 0% and 40%, less than 50%, less than 40%, less than 30%, less than 20%, or less than 10% of the area under the curve ($AUC_{0-\infty}$) for the plasma concentration of an inhaled corticosteroid (e.g., Pulmicort) having the same delivered dose (or dose adjusted for the same dose as administered orally).

Viscosity

In certain embodiments, compositions described herein have or are formulated to have a viscosity that is suitable for oral administration. In further embodiments, the compositions are have or are formulated to have a viscosity that is suitable for coating a portion (e.g., a targeted portion) of the gastrointestinal tract (e.g., esophagus).

Excipients, such as, for example, those listed herein, may be included in the composition to increase the viscosity of the delivered composition. The liquid viscosity may be increased in the oral form, or the excipient may increase the viscosity of the dissolved form of a tablet. Those of ordinary skill in the art will recognize that the viscosity should be at a level that is sufficient to deliver an effective amount of the composition to the esophagus, for example, in an amount that may coat the esophagus. Also, the viscosity should be at a level that may be given orally, thus not so thick that it is either too difficult to swallow, causes gagging, or is unpalatable. Those of ordinary skill in the art may determine the viscosity of the compositions provided in the Examples, and may thus determine appropriate ranges. One method of determining whether the composition is sufficiently viscous is by determining whether the inflammation, or eosinophilic infiltration, of the esophagus is reduced after treatment with the corticosteroid.

Viscosity can be determined by any method that will measure the resistance to shear offered by the substance or preparation. Many viscometers are available to those in the pharmaceutical field, and include those built by, for example, Brookfield. Viscosity may be, for example, measured at room temperature, at about 20-25 degrees Celsius, or at about 37 degrees Celsius to mimic body temperature. The viscosity of a liquid generally decreases as the temperature is raised. In some embodiments of the invention, the viscosity is about the viscosity of about 1 grams, about 2 grams, about 3 grams, about 4 grams, about 5 grams, about 6 grams, about 7 grams, about 8 grams, about 9 grams, about 10 grams, about 11 grams, about 12 grams, about 13 grams, about 14 grams, about 15 grams, about 1 to about 5 grams, about 1 to about 50 grams, or about 5 to about 25 grams of sucralose (Splenda®, Distributed By: McNeil Nutritionals, LLC, Fort Washington, Pa. 19034-2299), or about 7 to about 20 grams of sucralose (Splenda®), or about 5 to about 15 grams of sucralose (Splenda®), or about or about 7 to about 15 grams of sucralose (Splenda®), or about 8 to about 12 grams of sucralose (Splenda®), or about 10 to about 11 grams of (Splenda®), added to 4 ml water, at 25 degrees Celsius. In an illustrative embodiment, the viscosity is about the viscosity of 10 grams of sucralose (Splenda®) added to 4 ml of water, at 25 degrees Celsius. In other embodiments, the viscosity is about the viscosity of 5 to 20 grams of sucralose (Splenda®) in 8 ml total liquid volume, at 25 degrees Celsius. In other embodiments, the viscosity is about the viscosity of 5 to 15 grams of sucralose (Splenda®) in an 8 ml total liquid volume, at room temperature. In other embodiments, the viscosity is about the viscosity of 8 to 12 grams of sucralose (Splenda®) in an 8 ml total liquid volume at 25 degrees Celsius. In some embodiments, the viscosity is between that of about a fruit nectar and commercial honey, where the viscosity is measured at 25 degrees Celsius.

In some embodiments, the viscosity of the composition (e.g., at a shear rate of about 13.2 $sec^{-1}$) is at least 2 centipoise (cP), at least 5 cP, at least 10 cP, at least about 25 cP, at least about 30 cP, at least about 35 cP, at least about 40 cP, at least about 50 cP, about 2 cP to about 10 cP, about 2 cP to about 25 cP, about 2 cP to about 50 cP, about 20 cP to about 50 cP, about 20 cP to about 100 cP, or about 50 cP to about 100 cP. In some embodiments, the viscosity of the composition is at least about 100 cP. In certain embodiments, the viscosity of the composition, measured at about 25 degrees Celsius, is about 50 cP to about 250,000 cP, about 100 cP to about 250,000 cP, about 200 cP to about 250,000 cP, about 50 cP to about 70,000 cP, about 100 cP to about 70,000 cP, about 200 cP to about 70,000 cP, about 50 cP to about 40,000 cP, about 100 cP to about 40,000 cP, about 200 cP to about 40,000 cP, about 50 cP to about 25,000 cP, about 100 cP to about 25,000 cP, about 200 cP to about 25,000 cP, about 50 cP to about 10,000 cP, about 100 cP to about 10,000 cP, about 200 cP to about 10,000 cP, about 50 cP to about 3,000 cP, about 100 cP to about 3,000 cP, about 200 cP to about 3,000 cP, about 50 cP to about 2,000 cP, about 100 cP to about 2,000 cP or about 200 cP to about 2,000 cP. In one aspect, the viscosity of the composition, as measured at about 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition may range from about 100 cP to about 200 cP, about 200 cP to about 300 cP, about 250 cP to about 600 cP or about 400 cP to about 600 cP. In specific embodiments, the viscosity of the formulation is about 30 cP, about 100 cP, about 200 cP, about 300 cP, about 400 cP, about 500 cP, or about 250,000 cP (e.g., as measured with a Brookfield viscometer at 25 or 37 degrees Celsius equipped with an ultra low adapter). In certain instances, viscosity measurements are measured at a shear rate of 13.2/sec. In some instances, the gap between the spindle and the holder is 6 mm or greater.

In certain embodiments, the viscosity enhancing agent is provided in an amount sufficient to provide exposure of the corticosteroid to a gastrointestinal surface (e.g., esophagus) for a sufficient period of time such that the symptoms of and/or inflammation associated with allergic and/or caustic inflammatory disorders involving the gastrointestinal tract (e.g., of the esophagus) are reduced following administration of the corticosteroid containing oral dosage form as single dose or multiple dose administration.

In some embodiments, the viscosity of the composition is measured at room temperature (about 25 degrees C.) with a shear rate of about 13.2 sec$^{-1}$ (e.g., with a gap between the spindle and the sample chamber wall of about 6 mm or greater). In certain embodiments, provided herein is a composition having a viscosity under such conditions that is at least 2 centipoise (cP), at least 5 cP, at least 10 cP, at least about 25 cP, at least about 205 centipoise (cP), at least about 210 cP, at least about 220 cP, at least about 225 cP, at least about 250 cP, at least about 300 cP, or at least about 400 cP. In some embodiments, the viscosity of the composition under such conditions is about 50 cP to about 250,000 cP, about 50 cP to about 70,000 cP, about 50 cP to about 25,000 cP, about 50 cP to about 10,000 cP, about 50 cP to about 3,000 cP, about 50 cP to about 2,000 cP, about 250 cP to about 250,000 cP, about 250 cP to about 70,000 cP, about 250 cP to about 25,000 cP, about 250 cP to about 10,000 cP, about 250 cP to about 3,000 cP, or about 250 cP to about 2,000 cP. In one aspect, the viscosity of the composition, as measured at about 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition under such conditions may range from about 100 cP to about 200 cP, about 200 cP to about 300 cP, about 250 cP to about 600 cP or about 400 cP to about 600 cP. In specific embodiments, the viscosity of the formulation measured under such conditions is about 30 cP, about 40 cP, about 100 cP, about 200 cP, about 300 cP, about 400 cP, about 500 cP, or about 250,000 cP.

In some embodiments, the viscosity of the composition is measured at room temperature (about 25 degrees C.) with a shear rate of about 15 sec$^{-1}$ (e.g., with a gap between the spindle and the sample chamber wall of about 6 mm or greater). In certain embodiments, provided herein is a composition having a viscosity under such conditions that is at least 2 centipoise (cP), at least 5 cP, at least 10 cP, at least about 25 cP, at least about 150 centipoise (cP), at least about 50 cP, at least about 80 cP, at least about 100 cP, at least about 120 cP, at least about 150 cP, at least about 160 cP, at least about 170 cP, at least about 180 cP, at least about 190 cP, at least about 200 cP, about 100 cP, about 120 cP, about 150 cP, about 160 cP, about 170 cP, about 180 cP, about 190 cP, or about 200 cP. In some embodiments, the viscosity of the composition under such conditions is about 50 cP to about 250,000 cP, about 100 cP to about 250,000 cP, about 150 cP to about 250,000 cP, 160 cP to about 250,000 cP, 170 cP to about 250,000 cP, 180 cP to about 250,000 cP, or 190 cP to about 250,000 cP. In certain embodiments, the viscosity of the composition under such conditions is about 150 cP to about 70,000 cP, 160 cP to about 70,000 cP, 170 cP to about 70,000 cP, 180 cP to about 70,000 cP, or 190 cP to about 70,000 cP. In some embodiments, the viscosity of the composition under such conditions is about 150 cP to about 25,000 cP, 160 cP to about 25,000 cP, 170 cP to about 25,000 cP, 180 cP to about 25,000 cP, or 190 cP to about 25,000 cP. In certain embodiments, the viscosity of the composition under such conditions is about 150 cP to about 10,000 cP, 160 cP to about 10,000 cP, 170 cP to about 10,000 cP, 180 cP to about 10,000 cP, or 190 cP to about 10,000 cP. In some embodiments, the viscosity of the composition under such conditions is about 150 cP to about 3,000 cP, 160 cP to about 3,000 cP, 170 cP to about 3,000 cP, 180 cP to about 3,000 cP, or 190 cP to about 3,000 cP. In some embodiments, the viscosity of the composition under such conditions is about 150 cP to about 2,000 cP, 160 cP to about 2,000 cP, 170 cP to about 2,000 cP, 180 cP to about 2,000 cP, or 190 cP to about 2,000 cP. In certain embodiments, the viscosity of the composition under such conditions is about 25 cP to about 1,000 cP, about 50 cP to about 1,000 cP, about 80 cP to about 1,000 cP, about 100 cP to about 1,000 cP, about 120 cP to about 1,000 cP, about 150 cP to about 1,000 cP, about 25 cP to about 800 cP, about 50 cP to about 800 cP, about 80 cP to about 800 cP, about 100 cP to about 800 cP, about 120 cP to about 800 cP, about 150 cP to about 800 cP, about 25 cP to about 600 cP, about 50 cP to about 600 cP, about 80 cP to about 600 cP, about 100 cP to about 600 cP, about 120 cP to about 600 cP, about 150 cP to about 600 cP, about 25 cP to about 400 cP, about 50 cP to about 400 cP, about 80 cP to about 400 cP, about 100 cP to about 400 cP, about 120 cP to about 400 cP, or about 150 cP to about 400 cP.

In certain embodiments, a pharmaceutical composition described herein is a non-newtonian fluid. In some specific embodiments, the non-newtonian fluid is thixotropic. In certain embodiments, the non-newtonian fluid composition thins with shear, and thickens upon the absence of shear.

EXAMPLE 1

Patient 1 was a 6-year-old male with a history of abdominal pain, failure to thrive, and vomiting since infancy, and developmental delay with isolated EE diagnosed in 2001. His allergic history was significant for allergic rhinitis secondary to cat, dog, and dust mite exposure as well as positive Pharmacia CAP radioallergosorbent testing for fish and milk. Following upper gastrointestinal endoscopy (EGD) with esophageal biopsies demonstrating a maximum eosinophil count of 60 per high-powered field (hpf at 400× magnification) he was diagnosed with EE and treated with oral corticosteroid (prednisone 0.5 mg per kg daily) for one month. This resulted in resolution of esophageal eosinophilia with a maximum of 2 eosinophils per hpf on repeat EGD with biopsy. He was subsequently treated with omeprazole (Prilosec®) 10 mg twice daily and fluticasone (Flovent®) 220 ug twice daily as topical esophageal therapy but repeat EGD with biopsy after 6 months demonstrated a maximum eosinophil count of 50 per hpf. His therapeutic regimen was changed to elemental formula and fluticasone but repeat EGD with biopsy demonstrated persistent esophageal eosinophils with a maximal eosinophil count of 74 per hpf accompanied by basal zone hyperplasia. He was referred to Children's Hospital Eosinophilic Gastrointestinal Disorders clinic for further management of EE recalcitrant to usual therapy. At the time of his referral, he continued to have vomiting and poor weight gain and his mother reported significant difficulty with the puff and swallow technique. He was placed on a regimen of twice daily oral budesonide suspension (Pulmicort®) 500 micrograms (4 ml) mixed with about 10 packets (1 gram each) sucralose (Splenda®), a non-absorbed sugar in order to increase fluid viscosity to be swallowed twice daily. The total volume of the preparation was about 7 to 8 ml. Following 3 months of therapy, repeat EGD showed a normal esophagus and biopsies demonstrated complete resolution of both esophageal eosinophils and basal zone hyperplasia. In addition, his abdominal pain and vomiting resolved, resulting in increased appetite with documented weight gain. Eight am cortisol was 13.2 mcg/dL (normal range for age 3-15 mcg/dL) after four months of therapy.

EXAMPLE 2

Patient 2 was a 5-year-old girl with a history of developmental delay, abdominal pain, and RAST positivity for milk, egg, and wheat. EGD showed a normal esophagus but histopathology of biopsies demonstrated maximal eosinophil counts of 40 per hpf and basal zone hyperplasia. She was placed on a hydrolyzed formula containing milk protein (Peptamen Jr®), omeprazole 10 mg twice daily and oral cromolyn (Gastrocrom®) 100 mg four times daily. Following 12 months of therapy, repeat EGD demonstrated a pale, furrowed esophagus with maximum eosinophil counts of 94, 65, and 90 per hpf and diffuse basal zone hyperplasia in the distal, mid, and proximal esophagus, respectively. She was referred to the Children's Hospital Eosinophilic Gastrointestinal Disorders clinic for further management. Subsequent skin prick testing showed a positive response to her hydrolyzed milk protein containing formula and her diet was changed to elemental formula. After two months of elemental formula and oral cromolyn sodium, EGD was unchanged with a pale, furrowed esophagus and maximal eosinophil counts of 100, 90, and 70 per hpf in the distal, mid, and proximal esophagus with diffuse basal zone hyperplasia. Her developmental delay precluded the use of a fluticasone inhaler devise with puff and swallow technique. As an alternative, she received oral budesonide 500 micrograms (Pulmicort®) mixed with sucralose (Splenda®) twice daily as topical esophageal therapy. Following 3 months of budesonide, she had improvement in her abdominal pain and EGD revealed a normal appearing esophagus with improved maximum eosinophil counts of 28, 20, and 5 per hpf in the distal, mid, and proximal esophagus and decreased basal zone hyperplasia.

EXAMPLE 3

Multi-Patient Retrospective Review

This example details the efficacy and safety of once daily oral viscous budesonide (OVB) in inducing and maintaining remission of disease activity in children with EE. The results of this study show that in 20 children (mean age 5.5 yrs) the mean highest eosinophil count was 87 eos/hpf (range 30-170) before and 7 eos/hpf (range 0-50, $p<0.0001$) after therapy. There were 16 (80%) responders, 1 partial-responder and 3 non-responders. The mean symptom score fell from 4.4 to 0.8 ($p<0.0001$) and the mean endoscopy score from 3.6 to 0.8 ($p<0.0001$). No significant adverse events were reported. Morning cortisol levels were within normal limits.

Methods.

This retrospective review was approved by Children's Hospital, San Diego (CHSD) and University of California at San Diego (UCSD), Human Research Protection Program. Patients were referred from CHSD subspecialty clinics and other institutions to the EE clinic. Some patients received previous therapy with proton pump inhibitor, elimination diet based upon skin or blood allergy testing, elimination diet or topical fluticasone proprionate only after the diagnosis of EE was established. Patients who received these therapies, refused elimination diet, or were unable to utilize fluticsone prorionate MDI but continued to have $\geq 24$ eos/hpf on esophageal biopsy were offered OVB. Patients were defined as having food or aeroallergen sensitization if RAST and/or skin prick testing were positive. No changes were made to long-standing therapy used for treating chronic conditions such as asthma or eczema and none of the children received concurrent immune-modulatory treatment. Morning cortisol measurements were available only in 13 patients as this test was not initially performed routinely.

Upper Gastrointestinal Endoscopy and Biopsy. Endoscopy was performed using the Olympus P160 endoscope (by RD) and pan-esophageal, gastric and duodenal biopsies were taken. Eosinophilic esophagitis was diagnosed when $\geq 24$ eos/hpf were found in at least one of the esophageal sites biopsied. Two mucosal biopsies were taken from the proximal esophagus (3 cm below the crycopharyngeus muscle), distal esophagus (3 cm above the gastroesophageal junction (GEJ), and mid-esophagus (midpoint between the crycopharyngeus muscle and the GEJ). Biopsies were processed routinely and evaluated by a pediatric pathologist (RN). The highest number of eosinophils per ×400 high power field were counted [FIG. 1]. Basal zone hyperplasia (BZH) is reported when basal zone cells extend towards the luminal surface of the epithelium (>25% of epithelial thickness).

Follow-up endoscopy with biopsies were taken after 3-4 months treatment OVB. Counting the highest number of eos/hpf within biopsies determined the response to therapy and patients were categorized into responders (0-7 eos/hpf), partial-responders (8-23 eos/hpf) and non-responders ($\geq 24$ eos/hpf).

An EE Endoscopy Score was devised to compare findings before and after treatment. It was calculated from procedure reports and photographs. Four categories, (1) pallor and diminished vascular markings; (2) furrowing with "thickened" mucosa; (3) white mucosal plaques; (4) concentric rings or strictures. For each category, one point was allocated if 1 or 2 esophageal sites were involved, and two points for pan-esophageal involvement. The maximum score was 8.

Treatment. Patients received OVB 0.5 to 2 mg daily and were instructed not to ingest any solids or liquids for 30 minutes afterwards. Viscous budesonide was made by mixing each 0.5 mg Pulmicort™ respule with 5 grams (5 packets) of sucralose (Splenda™) to create a volume of 8-12 ml. A Pulmicort Respule™ is liquid budesonide intended for nebulized administration (0.5 mg budesonide/2 ml). No dietary changes were made in patients already on dietary restrictions. All patients received concurrent acid-suppression therapy.

Symptoms. A modified symptom score based on children with acid-peptic disease is used routinely in the EE clinic (31). The symptom categories include (1) heartburn or regurgitation; (2) abdominal pain or unexplained irritability in younger children; (3) nausea or vomiting; (4) anorexia or early satiety; (5) dysphagia or odynophagia, (6) nocturnal wakening with symptoms; (7) gastrointestinal bleeding (previous 4 months). Each category scored 0-2 points with a maximum of 14 points. Zero points were awarded if the symptom was absent; one point if the symptom was mild, did not interfere with daily activities; 2 points if the symptoms were severe enough to interrupt daily activities. Previous GI bleeding was considered mild (1 point) if there was no associated hemodynamic compromise or anemia, and severe (2 points) if bleeds were multiple, caused anemia, or required blood transfusion.

Statistical Analysis.

All statistical analysis was carried out using NCSS Statistical Softward Package. Two-tailed p values were calculated using paired t-tests to compare the means of patient values for eos/hpf, EE Endoscopy Scores and Symptom Scores before and after budesonide therapy. Two-tailed unpaired t-tests were utilized in order to compare variables grouped by responders versus non-responders. Spearman's correlation coefficients were generated using GraphPad Prism software. Results with p values <0.05 were considered statistically significant. Both mean and median statistics were generated, both were equivalent and mean statistics are presented.

Results.

Subjects. Chart reviews were undertaken on twenty children with a mean age of 5.5 years (range 1.7 to 17.6 yrs). Fifteen were Caucasian, 2 Hispanic, 2 Asian, and 1 African American. Three children had developmental delay (1 cerebral palsy, 1 autism, 1 Rett's Syndrome) and one had mild IgG deficiency (321 mg/dl, reference range 423-1090 mg/dl). None had *H. pylori* infection. Fourteen children had asthma, eczema and/or allergic rhinitis, 16 had sensitization to foods based on positive skin and/or RAST testing (Table 1). Prior to OVB, 6 children received a restriction diet (3 with concurrent elemental formula), 5 received topical fluticasone proprionate and 5 children received proton pump inhibitor (PPI) therapy. An additional 5 children received PPI therapy with either fluticasone proprionate or diet. All of these previously treated children had >24 eos/hpf on repeat esophageal biopsy before starting OVB therapy. [Table 1].

Mean morning cortisol levels measured in 18 patients was 9.5 ug/dL (patient range 6-17 ug/dL, normal range 2-17 ug/dL). Seventeen children gained weight during treatment at a mean rate of 0.42 kg/month. No adverse effects attributable to OVB were noted except for one child with low IgG who developed esophageal candida.

Treatment. Patients received OVB for a mean of 3.6 months before repeat endoscopy. Fifteen patients received OVB 1 mg/day, four received 2 mg/day and one unintentionally received 0.5 mg/day [Table 1]. In some embodiments of the invention, 0-1 mg/day, 1-2 mg/day, 2-3 mg/day, 34 mg/day, 4-5 mg/day, or 5-6 mg/day of corticosteroid, for example topical corticosteroid, for example, Budesonide, are administered to a patient.

Histology. Before treatment the mean highest eosinophil count for all patients, for all sites was 87 eos/hpf (95% CI 72-103), with a mean of 80 eos/hpf (95% CI 66-94) in the distal, 53 eos/hpf (95% CI 37-68) in the mid and 43 eos/hpf (95% CI 24-61) in the proximal esophagus. The highest eosinophil count was found in distal esophageal biopsies in 14, mid-esophageal in 3 and proximal esophageal biopsies in 3 patients. Ten patients (50%) had pan-esophageal BZH. The mean highest gastric and duodenal eosinophil count was 1 eos/hpf (range 0-5). Following treatment, the mean highest eosinophil count for all patients was 7 eos/hpf (95% CI 1-13, p<0.0001). All patients had a decreased eosinophil count with mean levels of 9 (95% CI 9-14) in distal, 5 (95% CI 1-9) in mid and 2 eos/hpf (95% CI 1-5) in the proximal esophagus. Sixteen patients were histologic responders, 1 partial-responder and 3 were non-responders (Table 1 and 2). There was no difference in age, height, dose, or duration of therapy between the 16 histologic responders and the 4 partial or non-responders. One partial-responder had received OVB 0.5 mg/day; his highest count fell from 100 to 16 eos/hpf. The three non-responders still demonstrated 50-80% improvement in their highest counts with treatment (Tables 1 and 2). Of the 5 patients who were non-responders to fluticasone proprionate, 3 were histologic responders, 1 was a partial-responder and 1 was a non-responder to OVB therapy; the non-responder still had a >70% drop in highest eosinophil count during treatment [Table 1].

Basal zone hyperplasia resolved completely in 6 of the 10 children with pan-esophageal findings. These patients were all histologic responders (Table 1).

Upper Gastrointestinal Endoscopy. Before treatment, the mean EE Endoscopy Score for all patients was 3.6 (range 1-6). The commonest findings were pallor (90%), linear furrowing (80%) and white plaques (50%). Following treatment the mean EE Endoscopy Score was 0.8 (range 0-5). The EE Endoscopy Score fell to 0 in twelve children and improved in nineteen. Eleven with complete normalization were histologic responders and 1 was a non-responder (>70% fall in eosinophil count). One child with an EE Endoscopy Scores that did not improve was a histologic non-responder. (Tables 1, 2, 3).

Symptom Score. Before treatment the mean symptom score for all patients was 4.4 and following treatment fell to 0.8 (p<0.0001). Eighteen children had an improved symptom score and 11 had a score of 0. Eight of these 11 patients were histologic responders with complete endoscopic resolution. Two children had symptom scores of 0 before and after OVB therapy. Although these 2 children had symptom resolution on elimination diet or fluticasone, histologic resolution did not occur until after treatment with OVB. The 5 patients who took only PPI therapy prior to budesonide did not have a significant improvement of symptoms on acid-suppression therapy alone (Tables 1, 2, 4).

There was a statistically significant correlation between the number of eosinophils and the Endoscopy and Symptom scores (Spearman® of 0.64 and 0.84 for the maximum eosinophil count and Symptom and Endoscopy score, respectively [p<0.0001]).

Discussion.

Eosinophilic esophagitis is a disorder of the esophagus which is becoming increasingly recognized (8, 14, 16, 17, 32-35). The annual incidence of the condition has been estimated at 1 in 10,000 children (35), but even this number may be an underestimate. The pathogenesis of EE is still poorly understood; allergic and abnormal host immunologic responses have been suggested. Therapeutic treatment options for EE have included dietary restriction/elemental diet, systemic and topical corticosteroids (2, 22-30). There is, however, presently no topical steroid designed for esophageal drug therapy. Twice daily ingested fluticasone propionate administered through an MDI is currently the most widely accepted topical therapy for EE. This therapy, however, may be particularly problematic for younger children and those with developmental delay who are unlikely to utilize the puff and swallow technique effectively (36). In this example, 10 of 13 children who were under the age of 5 and/or had developmental delay were responders to OVB therapy. The 3 non-responders still demonstrated a 50-80% reduction in esophageal eosinophil count; all had symptomatic improvement and 2 had endoscopic improvement. In addition to this, of the 5 children (ages 3-9 yrs) who previously failed to respond to swallowed fluticasone proprionate therapy, 3 had pan-esophageal histologic normalization with OVB and the other 2 had >75% reduction in esophageal eosinophil count.

These data suggest that following OVB therapy there is a strong correlation between the fall in esophageal eosinophil levels and the improvement in the Endoscopy and Symptom Score. This suggests that these scoring tools are useful clinical measures in pediatric EE but further prospective studies will need to be done in order to validate these tools. Eighteen (90%) of the patients, including the partial-responder and one non-responder, had improved Endoscopy Scores and all symptomatic children had improved Symptom Scores. This may be because the partial-responder and even the three non-responders had a 50-80% reduction in their highest esophageal eosinophil count following OVB treatment. The correlation between the severity of symptoms and of esophageal eosinophilic infiltration is not always so clear-cut. Two initially symptomatic children (#7 and 13, table 1) were asymptomatic before budesonide therapy despite having continued esophageal eosinophilic infiltration (80-120 eos/hpf). One child was a histologic non-responder to elimination diet and the other to topical fluticasone proprionate with PPI therapy, both for 3 months. These two children remained asymptomatic during budesonide therapy. This disassociation between symptoms and histologic disease is not unique to these two study patients. In our practice we have treated adolescents who, having initially responded symptomatically and histologically to ingested fluticasone proprionate, became non-compliant to therapy, claimed to be asymptomatic, but on routine follow-up evaluation had endoscopic and histologic recurrence of disease. The exact reason for this remains unclear. Children may become accustomed to their symptoms and not complain. Alternatively, they may conceal their symptoms because of an unwillingness to continue therapy or fear of undergoing further tests such as endoscopy. Another possibility is that eosinophilic infiltration may not always cause symptoms, even within the same individual. This could explain why some patients only complain of symptoms after esophageal structuring has occurred.

Most patients with EE are thought to have allergy-mediated disease, triggered by food and/or aeroallergens (2-4). However, 20% of the study patients had no evidence of IgE-mediated sensitization to foods or aeroallergens, and this concurs with other reported estimates of EE occurring in non-atopic individuals (17, 21, 35). Skin and patch testing can suggest causative food allergens in over half of the patients with EE, but not all will respond symptomatically or histologically to dietary restrictions (22). Amino-acid based formulas have been shown to be effective (2, 24, 37), but many children find the formula non-palatable and often require feeding through a naso-gastric or gastrostomy tube. In addition, after re-introducing new foods to children on elemental diets, patients require regular repeat UGI endoscopy to confirm continued control of inflammation. This example shows that children with EE, both with and without identifiable food/aero allergies respond well to OVB therapy and most are able to tolerate entirely normal diets. The dosing of OVB was based upon the therapeutic recommendations for asthmatic children. Most of the patients responded to 1 mg daily, but two patients needed 2 mg a day before a response was seen. All patients tested, including those taking OVB 2 mg daily, had normal morning cortisol levels and were therefore unlikely to have significant adrenal suppression. This may be because budesonide absorbed intestinally undergoes rapid hepatic metabolism.

Although there is conflicting data from pediatric and adult studies, with reports of negative 24 hr pH studies in children with EE, many patients will have at least a partial symptomatic response to acid-suppression therapy (1, 7, 17, 30, 38). Acid-suppression therapy alone will not, however, significantly alter the histologic findings and persisting esophageal eosinophilia may ultimately lead to esophageal narrowing in 10-30% of cases (14, 18, 20, 21). This lack of histologic response to PPI therapy in patients with EE was confirmed in 10 of the study patients. Before starting all patients on OVB therapy, eosinophils were more abundant and basal zone hyperplasia more prominent in distal, as compared with mid and proximal esophageal biopsies (80, 53 and 43 eos/hpf, respectively for tissue eosinophils and 95%, 75% and 65% of biopsies for BZH, respectively). The reason for this distal-predominance is unclear, but most likely supports the argument that GER does co-exist with EE, particularly as BZH and mild tissue eosinophilia also occur in reflux esophagitis. Therefore, all patients treated with OVB also received acid-suppression therapy.

These data suggest that oral viscous budesonide would be an effective and safe treatment for individuals, for example children, for example, young children, with proven EE. It may have advantages over other therapies in that it is palatable, its volume (8-12 ml) provides pan-esophageal mucosal coverage and it requires only once daily administration A larger placebo-controlled clinical trials would provide more information about dosing, efficacy and long-term safety of this treatment.

EXAMPLE 4

Figure 5:
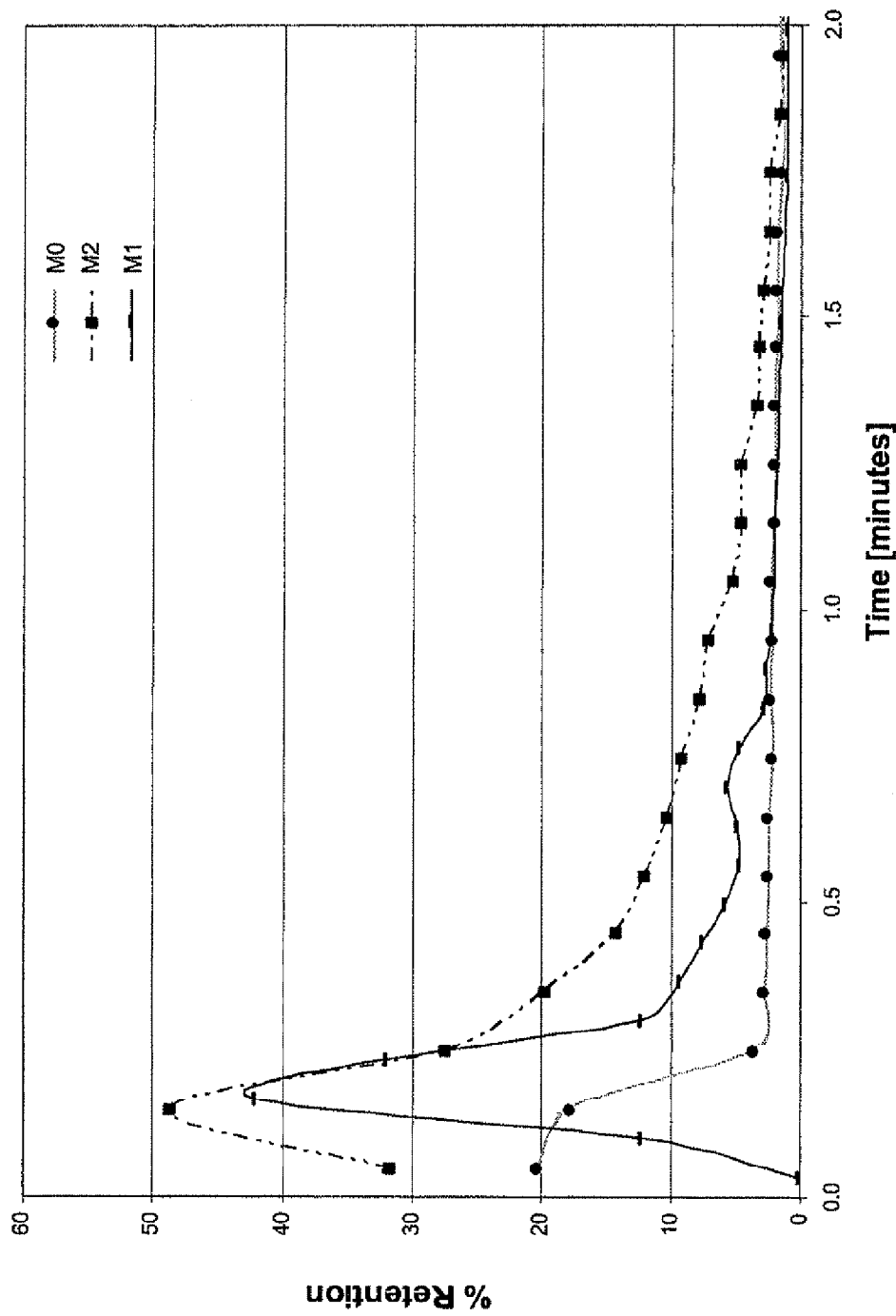
FIG. 5: Illustrates the percent amount of composition present in the esophagus as a function of time following oral administration (by measuring the amount of radiolabel present in the esophagus).

This example illustrates the increased interaction between a viscous composition described herein and the esophagus when compared to a radiolabeled oral composition made by combining Pulmicort Respules® (4 mL) with $^{99m}$Tc pertechnetate, and diluting with saline to about 7-8 mL (M0). The M0 compositions has a viscosity of about 1 cP at 13 sec$^{-1}$. Administered to a population of healthy individuals was a radiolabeled oral viscous budesonide composition (M1). The radiolabeled oral viscous budesonide composition (M1) was made in a volume of about 7-8 mL by combining Pulmicort Respules®, about 10 packets of Splenda®, and $^{99m}$Tc pertechnetate, and has a viscosity of about 200 cP at 13 sec$^{-1}$. The radiolabeled oral viscous budesonide composition (M2) was made in a volume of about 7-8 mL by combining Pulmicort Respules®, 70% w/w maltodextrin, and $^{99m}$Tc pertechnetate, having a viscosity of about 1450 cP at 13 sec$^{-1}$. Also administered to a population of healthy individuals was a radiolabeled oral non-viscous budesonide composition. Increased interaction of the oral viscous budesonide composition was determined by measuring the amount of radiolabel present in the esophagus following oral administration of the oral viscous budesonide composition. FIG. 5 illustrates the percent amount of composition present in the esophagus as a function of time following oral administration (by measuring the amount of radiolabel present in the esophagus).

The area under the curve (AUCr) of the percent of the dose administered as a function of time (% dose·time(min)) was determined from the time of 50% swallow (i.e., 50% of the administered dose had passed from the mouth), until esophageal activity had peaked and fallen to 10% of the peak value. The area under the curve from t=0 min to t=1 min (AUC$_{0-1}$); and from t=0 min to t=2 min (AUC$_{0-2}$) was also determined. These results (including the ratio of the non-viscous sample to the viscous sample) are set forth below:

| Formulation | AUCr geometric mean | ratio | AUC$_{0-1}$ geometric mean | ratio | AUC$_{0-2}$ geometric mean | ratio |
|---|---|---|---|---|---|---|
| M0 | 3.95 | | 5.51 | | 6.93 | |
| M1 | 6.33 | 0.62 | 8.84 | 0.62 | 9.41 | 0.74 |
| M2 | 17.67 | 0.22 | 18.91 | 0.29 | 21.94 | 0.32 |

EXAMPLE 5

Figure 4:
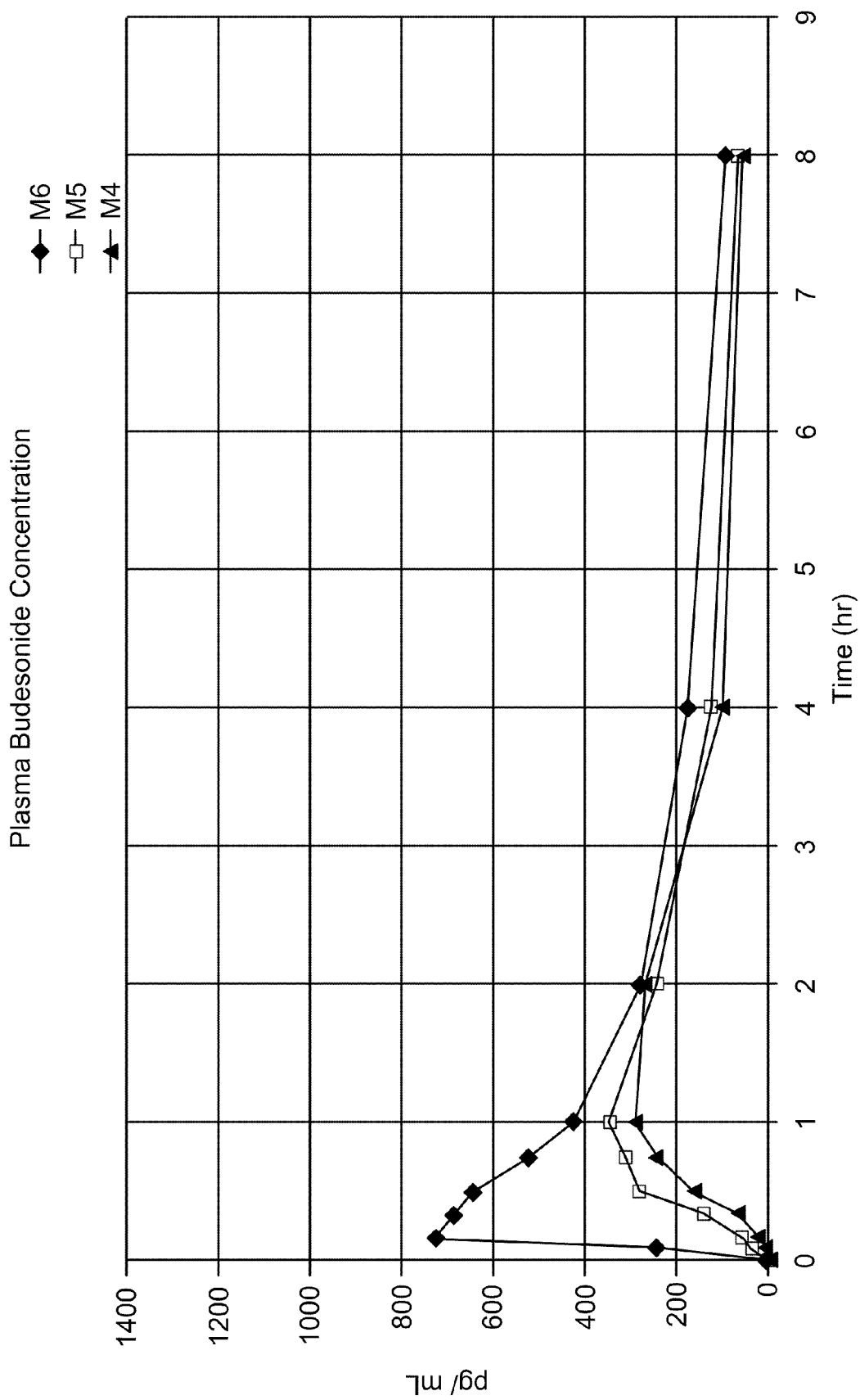
FIG. 4: Illustrates the reduced systemic affect of swallowing an oral composition described herein when compared to the administration of an inhaled corticosteroid composition.

This example illustrates the reduced systemic affect of swallowing an oral composition described herein when compared to the administration of an inhaled corticosteroid composition. Orally administered (by swallowing) was (1) a composition comprising 1 mg of budesonide (two 0.5 mg/2 mL Pulmicort Respules®) and about 10 grams of maltodextrin (and minor amounts of other additives) (M4); and (2) a composition comprising 1 mg of budesonide (two 0.5 mg/2 mL Pulmicort Respules®) diluted with water to a volume of about 8-12 mL (M5). Administered by inhalation (using an LC Plus® nebuliser) was 1 mg of budesonide (two 0.5 mg/2 mL Pulmicort Respules®) (M6). As illustrated in FIG. 4, oral administration of budesonide provided a significant decrease in AUC and Cmax values when compared to the inhaled administration of dose of budesonide having the same nominal amount of budesonide.

TABLE 1

Patient Characteristics pre- and post-viscous Budesonide (Budes.) therapy.

| Pt. | Age mths. | Res*** | Sex | ΔWt**** | IGE* | Prior** mths. | PPI before Budes. | Budes Dose mths. | Highest Eos. count/Hpf Site+ | Pre | Post | Basal Zone Hyperplasia (site*) Pre | Post | Endoscopy Score Pre | Post | Symptom Score Pre | Post |
|---|---|---|---|---|---|---|---|---|---|---|---|---|---|---|---|---|---|
| 1 | 42 | R | M | −0.1 | F, A | ELIM (4) | No | 1 mg (4) | M | 70 | 1 | Yes (P, M, D) | Yes (P, M) | 6 | 1 | 3 | 2 |
| 2 | 33 | R | M | 0.15 | X | | No | 1 mg (3) | D | 30 | 7 | Yes (D) | Yes (D) | 1 | 0 | 7 | 3 |
| 3 | 71 | R | M | 0.73 | F, A | | Yes | 1 mg (3) | D | 74 | 0 | Yes (P, D) | No | 2 | 0 | 5 | 0 |
| 4 | 109 | R | M | 0.85 | X | FLU (3) | Yes | 1 mg (4) | M | 100 | 2 | Yes (M, D) | No | 4 | 2 | 4 | 0 |
| 5 | 41 | R | M | −0.07 | F, A | ELIM (2) | Yes | 1 mg (3) | D | 50 | 0 | Yes (M, D) | No | 2 | 1 | 8 | 3 |
| 6 | 66 | | M | | F, A | FLU (3) | | 1 mg (3) | P | 60 | 50 | | | 6 | 1 | 4 | 3 |
| | | R | M | 0.5 | F, A | | Yes | 2 mg (3) | P | 50 | 0 | Yes (M) | No | 1 | 0 | 3 | 2 |
| 7 | 88 | | M | | F, A | FLU (12) | Yes | 1 mg (3) | D | 50 | 80 | | | 4 | 4 | 0 | 0 |
| | | R | | 0.375 | | | Yes | 2 mg (3) | D | 80 | 1 | Yes (P, M, D) | No | 4 | 0 | 0 | 0 |
| 8 | 90 | R | F | 0.63 | X | | No | 1 mg (4) | P | 170 | 0 | Yes (P, D) | No | 6 | 1 | 9 | 0 |
| 9 | 41 | R | M | 0.18 | A | | Yes | 1 mg (4) | P, D | 70 | 0,0 | Yes (P, M, D) | No | 2 | 0 | 3 | 0 |
| 10 | 20 | R | M | 0.03 | F | | Yes | 1 mg (4) | D | 80 | 0 | Yes (P, M, D) | No | 4 | 0 | 3 | 0 |
| 11 | 201 | R | F | 0.1 | A | | No | 2 mg (4) | D | 130 | 0 | Yes (P, M, D) | No | 6 | 0 | 5 | 1 |
| 12 | 34 | R | M | −0.15 | X | | No | 1 mg (3) | D | 100 | 0 | Yes (P, M, D) | No | 5 | 0 | 3 | 0 |
| 13 | 51 | R | F | 0.08 | F | ELIM (5) | No | 1 mg (6) | D | 120 | 0 | Yes (D) | No | 2 | 0 | 0 | 0 |
| 14 | 48 | R | M | 1.5 | F | ELIM (5) | No | 1 mg (3) | D, M, P | 30 | 0 | Yes (P, M, D) | No | 4 | 0 | 3 | 0 |
| 15 | 31 | R | M | 0.2 | F | ELIM (3) | Yes | 1 mg (4) | D | 100 | 5 | Yes (P, D) | No | 2 | 0 | 7 | 0 |
| 16 | 121 | R | M | 0.13 | F, A | | Yes | 2 mg (3) | M | 90 | 3 | Yes (P, M, D) | Yes (P, M, D) | 4 | 2 | 4 | 1 |
| 17 | 36 | P | M | 0.46 | F, A | FLU (12) | No | 0.5 mg (3) | D | 100 | 16 | Yes (M, D) | No | 6 | 1 | 6 | 2 |
| 18 | 32 | N | M | 0.83 | F | | No | 1 mg (3) | D | 100 | 50 | Yes (M, D) | Yes (P, D) | 2 | 3 | 3 | 1 |
| 19 | 68 | N | F | 0.15 | F | ELIM (2) | Yes | 1 mg (4) | D | 100 | 28 | Yes (P, M, D) | Yes (P, M, D) | 4 | 0 | 2 | 0 |

TABLE 1-continued

Patient Characteristics pre- and post-viscous Budesonide (Budes.) therapy.

| Pt. | Age mths. | Res*** | Sex | ΔWt**** | IGE* | Prior** mths. | PPI before Budes. | Budes Dose mths. | Highest Eos. count/Hpf Pre/Post Budesonide Site+ | Pre | Post | Basel Zone Hyperplasia (site*) Pre | Post | Endoscopy Score Pre | Post | Symptom Score Pre | Post |
|---|---|---|---|---|---|---|---|---|---|---|---|---|---|---|---|---|---|
| 20 | 93 | N | M | 0.15 | F, A | FLU | No | 1 mg (4) | D | 100 | 25 | Yes (P, M, D) | Yes (P, M, D) | 5 | 2 | 8 | 0 |

Patient response was determined by counting the highest eosinophil count/hpf after viscous budesonide and categorized into responders (0-7 eos/hpf), partial-responders (8-23 eos/hpf) and non-responders (≧24 eos/hpf).
Patient 6 and 7 failed treatment with 1 mg viscous budesonide, but responded to an increased dose. Patient 11 was started on 2 mg viscous budesonide because of her age and size. Patient 16 had dose increased from 1 mg to 2 mg viscous budesonide after one month because symptoms persisted on lower dose.
*Specific IgE. Sensitization to food (F) or aeroallergens (A) as determined by RAST or skin-prick testing. X = none.
**Prior therapy was with elimination diet (ELIM), topical fluticasone proprionate and/or proton pump inhibitors (PPI).
+Site of esophageal involvement is divided into distal (D), mid (M), and proximal (P).
***Response Category R = Responder, N = Non-Responder, P = Partial Responder.
****Weight change per month. mths = months.
The highest eosinophil count/hpf, presence of basal zone hyperplasia, endoscopy and symptom scores are given pre- and post-viscous budesonide therapy.
Maximum Endoscopy score is 8 and maximum Symptom Score is 14.

TABLE 2

Esophageal eosinophil count pre- and post-viscous budesonide for different patient response categories.

| Response Catergory | Esophagus Eos/hpf Mean (SEM) Pre | Post | Proximal Esophagus Eso/hpf Pre | Post | Mid Esophagus Eos/hpf Pre | Post | Distal Esophagus Eos/hpf Pre | Post |
|---|---|---|---|---|---|---|---|---|
| Responders N = 16 | 84 (9) | 1.4** (0.6) | 44 (11) | 1* (0.5) | 49 (8) | 1** (0.5) | 75** (8) | 3 (1) |
| Partial-responder N = 1 | 100 | 20 | 50 | 20 | 60 | ND | 100 | 16 |
| Non-responders N = 3 | 100 (0) | 34* (8) | 50 (25) | 6 (2) | 68 (17) | 19 (4) | 100 (0) | 34* (8) |

Mean values and standard error of mean (SEM) in parenthesis are provided for the highest esophageal eosinophil counts (eos/hpf) measured within the whole esophagus and different sites.
*p < 0.05
**p < 0.0001. Categories without asterisks do not reach statistical significance.

TABLE 3

Eosinophilic esophagitis Endoscopy Scores, pre- and post-viscous budesonide therapy, for different response categories.

| Response Category | Total Score Mean (SEM) Pre | Post | Pallor Mean (SEM) Pre | Post | Furrows Mean (SEM) Pre | Post | Plaques Mean (SEM) Pre | Post | Esophageal Rings Pre | Post |
|---|---|---|---|---|---|---|---|---|---|---|
| Responders N = 16 | 3.4 (0.4) | 0.4** (0.2) | 1.4 (0.2) | 0.3** (0.2) | 1.3 (0.2) | 0.2** (0.1) | 0.8 (0.2) | 0* (0) | None | None |
| Partial-responder N = 1 | 6 | 1 | 2 | 0 | 2 | 1 | 2 | 0 | None | None |
| Non-responder N = 3 | 3.7 (0.9) | 1.7 (0.9) | 1.7 (0.3) | 0.7* (0.3) | 1 (0.6) | 0.3 (0.3) | 1 (0.6) | 0.3 (0.3) | None | None |

Maximum total score is 8 and maximum for each category is 2.
Standard error of mean shown in parathesis.
*p < 0.05
**p < 0.001,
Categories without asterisks do not reach statistical significance.

TABLE 4

Symptom Score, pre- and post-viscous budesonide therapy for different response categories.

| Cat. | Total Score Mean (SEM) | | Heartburn | | Pain | | Nausea/Vomiting | | Dysphagia | | Nocturnal Wakening | | Anorexia | | GI Bleed | |
|---|---|---|---|---|---|---|---|---|---|---|---|---|---|---|---|---|
| | Pre | Post | Pre | Post | Pre | Post | Pre | Post | Pre | Post | Pre | Post | Pre | Post | Pre | Post |
| R N = 16 | 4.2 (0.6) | 0.75** (0.3) | 1 (0.2) | 0.1** (0.1) | 0.8 (0.2) | 0.2* (0.1) | 1.4 (0.2) | 0.1** (0.1) | 0.2 (0.1) | 0.1 (1) | 0.2 (0.2) | 0 (0) | 0.6 (0.2) | 0.3 (0.2) | None | none |
| P N = 1 | 6 | 2 | 2 | 1 | 2 | 1 | 2 | 0 | 0 | 0 | 0 | 0 | 0 | 0 | None | None |
| N N = 3 | 5.5* (0.5) | 0.5* (0.5) | 1.5 (0.5) | 0.5 (0.5) | 1.5 (0.5) | 0 (0) | 1.5 (0.5) | 0 (0) | 1 (1) | 0 (0) | 0 | 0 | 0 | 0 | None | None |

Maximum total score is 14 and maximum for each category is 2.
Standard error of mean shown in parenthesis.
*$p < 0.05$
**$p < 0.001$,
Categories without asterisks do not reach statiscal significance.
Cat.: Response Category,
R = Responders
P = Partial-Responder,
N = Non-Responders

REFERENCES

1. Liacouras C A, Ruchelli E. Eosinophilic esophagitis. Cuff. Opin. Pediatr. 2004; 16:560-6.
2. Kelly K J, Lazenby A J, Rowe P C, et al. Eosinophilic esophagitis attributed to gastroesophageal reflux: improvement with an amino acid-based formula. Gastroenterology 1995; 109: 1503-12.
3. Fogg M I, Ruchelli E, Spergel J M. Pollen and eosinophilic esophagitis. J. Allergy Clin. Immunol. 2003; 112:796-7.
4. Mishra A, Hogan S P, Brandt E B, Rothenberg M E. An etiological role for aeroallergens and eosinophils in experimental esophagitis. J. Clin. Invest. 2001; 107:83-90.
5. Spergel J M, Beausoleil J L, Mascarenhas M, Liacouras C A. The use of skin prick tests and patch tests to identify causative foods in eosinophilic esophagitis. J. Allergy Clin. Immunol. 2002; 109:363-8.
6. Ruchelli E, Wenner W, Voytek T, et al. Severity of esophageal eosinophilia predicts response to conventional gastroesophageal reflux therapy. Pediatr. Dev. Pathol. 1999; 2:15-8.
7. Steiner S J, Gupta S K, Croffie J M, Fitzgerald J F. Correlation between number of eosinophils and reflux index on same day esophageal biopsy and 24 hour esophageal pH monitoring. Am. J. Gastroenterol. 2004; 99:801-5.
8. Orenstein S R, Shalaby T M, Di Lorenzo C, et al. The spectrum of pediatric eosinophilic esophagitis beyond infancy: a clinical series of 30 children. Am. J. Gastroenterol. 2000; 95:1422-30.
9. Rothenberg M E, Mishra A, Collins M H, Putnam P E. Pathogenesis and clinical features of eosinophilic esophagitis. J. Allergy Clin. Immunol. 2001; 108:891-4.
10. Ravelli A M, Villanacci V, Ruzzenenti N, et al. Dilated Intercellular Spaces: A Major Morphological Feature of Esophagitis. J. Pediatr. Gastroenterol. Nutr. 2006; 42:510-515.
11. Steiner S J, Kernek K M, Fitzgerald J F. Severity of Basal Cell Hyperplasia Differs in Reflux Versus Eosinophilic Esophagitis. J. Pediatr. Gastroenterol. Nutr. 2006; 42:506-509.
12. Mueller S, Aigner T, Neureiter D, Stolte M. Eosinophil infiltration and degranulation in oesophageal mucosa from adult patients with eosinophilic oesophagitis: a retrospective comparative study on pathologic biopsy. J. Clin. Pathol. 2006; 59:1175-80.
13. Croese J, Fairley S K, Masson J W, et al. Clinical and endoscopic features of eosinophilic esophagitis in adults. Gastrointest. Endosc. 2003; 58:516-22.
14. Aceves S, Newbury, R O, Dohil R, Schwimmer J, Bastian J. Distinguishing Eosinophilic Esophagitis in pediatric patients: clinical, endoscopic, and histologic features of an emerging disorder. Journal of Clinical Gastroenterology 2006; 41(3):252-6.
15. Straumann A, Simon H U. Eosinophilic esophagitis: escalating epidemiology? J. Allergy Clin. Immunol. 2005; 115: 418-9.
16. Cherian S, Smith N M, Forbes D A. Rapidly increasing prevalence of eosinophilic oesophagitis in Western Australia. Arch. Dis. Child 2006; 91:1000-4.
17. Sant'Anna A M, Rolland S, Fournet J C, et al. Eosinophilic Esophagitis in Children: Symptoms, Histology and pH Probe Results. J. Pediatr. Gastroenterol. Nutr. 2004; 39:373-377.
18. Potter J W, Saeian K, Staff D, et al. Eosinophilic esophagitis in adults: an emerging problem with unique esophageal features. Gastrointest. Endosc. 2004; 59:355-61.
19. Parfitt J R, Gregor J C, Suskin N G, et al. Eosinophilic esophagitis in adults: distinguishing features from gastroesophageal reflux disease: a study of 41 patients. Mod. Pathol. 2006; 19:90-6.
20. Desai T K, Stecevic V, Chang C H, et al. Association of eosinophilic inflammation with esophageal food impaction in adults. Gastrointest. Endosc. 2005; 61:795-801.
21. Straumann A, Spichtin H P, Grize L, et al. Natural history of primary eosinophilic esophagitis: a follow-up of 30 adult patients for up to 11.5 years. Gastroenterology 2003; 125:1660-9.
22. Spergel J M, Andrews T, Brown-Whitehorn T F, et al. Treatment of eosinophilic esophagitis with specific food elimination diet directed by a combination of skin prick and patch tests. Ann. Allergy Asthma Immunol. 2005; 95:336-43.
23. Kagalwalla A F, Sentongo T A, Ritz S, et al. Effect of six-food elimination diet on clinical and histologic outcomes in eosinophilic esophagitis. Clin. Gastroenterol. Hepatol. 2006; 4:1097-102.
24. Markowitz J E, Spergel J M, Ruchelli E, Liacouras C A. Elemental diet is an effective treatment for eosinophilic esophagitis in children and adolescents. Am. J. Gastroenterol. 2003; 98:777-82.

25. Liacouras C A, Wenner W J, Brown K, Ruchelli E. Primary eosinophilic esophagitis in children: successful treatment with oral corticosteroids. J. Pediatr. Gastroenterol. Nutr. 1998; 26:380-5.
26. Teitelbaum J E, Fox V L, Twarog F J, et al. Eosinophilic esophagitis in children: immunopathological analysis and response to fluticasone propionate. Gastroenterology 2002; 122:1216-25.
27. Faubion W A, Jr., Perrault J, Burgart L J, et al. Treatment of eosinophilic esophagitis with inhaled corticosteroids. J. Pediatr. Gastroenterol. Nutr. 1998; 27:90-3.
28. Aceves S S, Dohil R, Newbury R O, Bastian J F. Topical viscous budesonide suspension for treatment of eosinophilic esophagitis. J. Allergy Clin. Immunol. 2005; 116: 705-6.
29. Noel R J, Putnam P E, Collins M H, et al. Clinical and immunopathologic effects of swallowed fluticasone for eosinophilic esophagitis. Clin. Gastroenterol. Hepatol. 2004; 2:568-75.
30. Remedios M, Campbell C, Jones D M, Kerlin P. Eosinophilic esophagitis in adults: clinical, endoscopic, histologic findings, and response to treatment with fluticasone propionate. Gastrointest. Endosc. 2006; 63:3-12.
31. Dohil R, Newbury R O, Sellers Z M, et al. The evaluation and treatment of gastrointestinal disease in children with cystinosis receiving cysteamine. J. Pediatr. 2003; 14:224-30.
32. Cheung K M, Oliver M R, Cameron D J, et al. Esophageal eosinophilia in children with dysphagia. J. Pediatr. Gastroenterol. Nutr. 2003; 37:498-503.
33. Fox V L, Nurko S, Furuta G T. Eosinophilic esophagitis: it's not just kid's stuff. Gastrointest. Endosc. 2002; 56:260-70
34. Budin C, Villard-Truc F, Rivet C, et al. [Eosinophilic esophagitis: 3 case reports]. Gastroenterol. Clin. Biol. 2005; 29:73-5.
35. Noel R J, Putnam P E, Rothenberg M E. Eosinophilic esophagitis. N. Engl. J. Med. 2004; 351:940-1.
36. Guajardo J R, Plotnick L M, Fende J M, et al. Eosinophil-associated gastrointestinal disorders: a world-wide-web based registry. J. Pediatr. 2002; 141:576-81.
37. Liacouras C A, Spergel J M, Ruchelli E, et al. Eosinophilic esophagitis: a 10-year experience in 381 children. Clin. Gastroenterol. Hepatol. 2005; 3:1198-206.
38. Liacouras C A. Eosinophilic esophagitis: treatment in 2005. Curr. Opin. Gastroenterol. 2006; 22:147-152.
39. Spergel J M. Eosinophilic esophagitis in adults and children: evidence for a food allergy component in many patients. Curr. Opin. Allergy Clin. Immunol. 2007; 7:274-8.
40. Plaza-Martin, A M, Jimenez-Feijoo R, Andaluz C, Giner-Munoz M T, Martin-Mateos M A, Piquer-Gibert M, Sierra-Martinez J I. Polysensitization to aeroallergens and food in eosinophilic esophagitis in a pediatric population. Alergol. Immunopathol. 2007; 35:35-7.
41. Nicolazzo, J A, Reed, B L, Finnin, B C. Buccal penetration enhancers—how do they really work? J. Controlled Release 2005; 105:1-15.
42. Furuta, G T, Liacouras, C A, Collins, M H, Sandeep, K G, Justinich, C, Putnam, P E, Bonis, P, Hassall, E, Straumann, A, Rothenberg, M E. Eosiniophilic esophagitis in children and adults: A systematic review and consensus recommendations for diagnosis and treatment. Gastroenterology 2007; 133:1342-1363.
43. Aceves, S S, Bastian J F, Newbury, R O, Dohil, R. Oral viscous budesonide: A potential new therapy for eosinophilic esophagitis. Amer. Journal of Gastroenterology 2007; 102:1-9.
44. Rothenberg M E. Eosinophilic gastrointestinal disorders. J. Allergy Clin. Immunol. 2004; 113:11-28.
45. Garrett J K, Jameson S C, Thomson B, Collins M H, Wagoner L E, Freese, D K, et al. Anti-interleukin-5 (mepolizumab) therapy for hypereosinophilic syndromes. J. Allergy Clin. Immunol. 2004; 113:115-9.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies which are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method of treating, reducing, or alleviating esophageal inflammation in an individual comprising orally administering to said individual a pharmaceutical composition, the composition comprising a corticosteroid, at least one viscosity enhancing excipient, and a liquid vehicle, and the composition having a viscosity of at least 2 cP.

2. The method of claim 1, wherein the pharmaceutical composition is a suspension comprising corticosteroid particles.

3. The method of claim 1, wherein the viscosity of the pharmaceutical composition is at least 10 cP at 25 degrees Celcius with a shear rate of about 13.2 sec$^{-1}$.

4. The method of claim 1, wherein the pharmaceutical composition is administered once a day, twice a day, or three times a day.

5. The method of claim 1, wherein the pharmaceutical composition is administered no more than once a day.

6. The method of claim 1, wherein said corticosteroid is a topical corticosteroid.

7. The method of claim 1, wherein said corticosteroid is Budesonide.

8. The method of claim 1, wherein the viscosity enhancing excipient is selected from the group consisting of lactose, sucrose, sucralose, maltodextrin, dextrose, mannitol, sorbitol, honey, maize starch, wheat starch, rice starch, potato starch, gelatin, gum tragacanth, methyl cellulose, hydroxypropylmethyl-cellulose, a carboxymethyl cellulose (CMC), sodium carboxymethyl-cellulose (NaCMC), polyvinylpyrrolidone (PVP: povidone), and combinations thereof.

9. The method of claim 1, wherein the esophageal inflammation is eosinophilic esophagitis.

10. The method of claim 1, wherein 0.5-10 mg corticosteroid per day is administered to said individual.

11. The method of claim 1, wherein oral administration of the pharmaceutical composition provides a decreased systemic load of corticosteroid, as measured by plasma $AUC_{0-\infty}$, when compared to inhaled administration delivering an identical amount of corticosteroid.

12. The method of claim 1, wherein the pharmaceutical composition comprises corticosteroid particles, wherein at least 95% of the corticosteroid particles have a diameter of less than 10 microns.

13. The method of claim 1, wherein said liquid vehicle comprises water.

* * * * *

UNITED STATES PATENT AND TRADEMARK OFFICE
CERTIFICATE OF CORRECTION

| | | |
|---|---|---|
| PATENT NO. | : 8,497,258 B2 | Page 1 of 1 |
| APPLICATION NO. | : 12/269693 | |
| DATED | : July 30, 2013 | |
| INVENTOR(S) | : Dohil et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 834 days.

Signed and Sealed this
Tenth Day of February, 2015

Michelle K. Lee
*Deputy Director of the United States Patent and Trademark Office*